United States Patent
Wojcik et al.

(10) Patent No.: US 9,829,480 B2
(45) Date of Patent: Nov. 28, 2017

(54) REMOTE BREATH ALCOHOL MONITOR

(71) Applicants: Mark Henry Wojcik, Littleton, CO (US); Gary Alan Shoffner, Centennial, CO (US); Gordon William Murray, Lone Tree, CO (US); Gregory Jerome Morton, Henderson, CO (US); Matthew Paul Zenthoefer, Centennial, CO (US)

(72) Inventors: Mark Henry Wojcik, Littleton, CO (US); Gary Alan Shoffner, Centennial, CO (US); Gordon William Murray, Lone Tree, CO (US); Gregory Jerome Morton, Henderson, CO (US); Matthew Paul Zenthoefer, Centennial, CO (US)

(73) Assignee: ALCOHOL MONITORING SYSTEMS, INC., Littleton, CO (US)

( * ) Notice: Subject to any disclaimer, the term of this patent is extended or adjusted under 35 U.S.C. 154(b) by 90 days.

(21) Appl. No.: 14/658,593

(22) Filed: Mar. 16, 2015

(65) Prior Publication Data
US 2015/0212063 A1   Jul. 30, 2015

Related U.S. Application Data

(63) Continuation-in-part of application No. 14/038,448, filed on Sep. 26, 2013.

(51) Int. Cl.
*G08B 23/00* (2006.01)
*G08B 13/14* (2006.01)
(Continued)

(52) U.S. Cl.
CPC ......... *G01N 33/4972* (2013.01); *A61B 5/082* (2013.01); *G06K 9/00261* (2013.01); *G06K 9/00268* (2013.01); *G01N 33/0075* (2013.01)

(58) Field of Classification Search
CPC .... B60K 28/063; B60K 28/06; B60K 28/066; B60K 35/00; B60W 2540/24;
(Continued)

(56) References Cited

U.S. PATENT DOCUMENTS

| 4,843,377 A | 6/1989 | Fuller et al. |
| 4,916,435 A | 4/1990 | Fuller |

(Continued)

FOREIGN PATENT DOCUMENTS

| GB | 2391218 | 2/2004 |
| JP | 2009-064139 | 3/2009 |

OTHER PUBLICATIONS

Screen captures of definitions of gallery captured Feb. 2, 2017, Merriam Webster and Reverso Collins.*

(Continued)

*Primary Examiner* — Emily C Terrell
(74) *Attorney, Agent, or Firm* — Stanley J. Gradisar Attorney At Law, LLC; Stanley J. Gradisar

(57) ABSTRACT

A portable handheld wireless breath alcohol monitoring device (RBAM) utilizes facial recognition from an enrollment image or gallery of images accumulated over time, and automatic retesting if an initial test is positive for alcohol or of an initial facial match is negative. A location fix is captured with each breath test taken by an offender. After each breath test, the breath alcohol content (BrAC), date and time of the breath test, facial image data, and location fix are uploaded through a built-in cellular phone module in the RBAM to a monitoring station. The monitoring station evaluates each breath test and determines if immediate notification to a supervising agency is needed. If so, an email, text message, or page is sent to the supervising agency. RBAM enables the monitoring of lower-risk offend- (Continued)

ers or offenders who have earned the privilege of a less intrusive alcohol testing and monitoring program.

34 Claims, 14 Drawing Sheets

(51) Int. Cl.
| | |
|---|---|
| G08C 15/06 | (2006.01) |
| G01N 33/497 | (2006.01) |
| G06K 9/00 | (2006.01) |
| A61B 5/08 | (2006.01) |
| G01N 33/00 | (2006.01) |

(58) Field of Classification Search
CPC ..... B60W 2540/28; B60W 2040/0836; B60W 2540/22; B60W 40/08
USPC .................. 340/573.1, 576, 870.02
See application file for complete search history.

(56) References Cited

U.S. PATENT DOCUMENTS

| | | | |
|---|---|---|---|
| 4,999,613 A | 3/1991 | Williamson et al. | |
| 6,108,437 A | 8/2000 | Lin | |
| 6,433,863 B1 | 8/2002 | Weiss | |
| 6,726,636 B2 | 4/2004 | Der Ghazarian et al. | |
| 6,748,792 B1* | 6/2004 | Freund | B60K 28/063 180/272 |
| 6,837,095 B2 | 1/2005 | Sunshine et al. | |
| 6,923,040 B2 | 8/2005 | Stock | |
| 6,956,484 B2 | 10/2005 | Crespo | |
| 6,967,581 B2 | 11/2005 | Karsten | |
| 7,341,693 B2 | 3/2008 | Der Ghazarian et al. | |
| 7,462,149 B2 | 12/2008 | Hawthorne et al. | |
| 7,492,943 B2 | 2/2009 | Li et al. | |
| 7,542,624 B1 | 6/2009 | Koch | |
| 7,641,611 B2 | 1/2010 | Hawthorne et al. | |
| 7,800,687 B2 | 9/2010 | Khan et al. | |
| 7,823,681 B2* | 11/2010 | Crespo | A61B 5/082 180/272 |
| 7,891,456 B2 | 2/2011 | Takahashi et al. | |
| 7,934,577 B2 | 5/2011 | Walter et al. | |
| 7,956,890 B2 | 6/2011 | Cheng et al. | |
| 8,165,282 B1 | 4/2012 | Coughlan et al. | |
| 8,165,352 B1 | 4/2012 | Mohanty et al. | |
| 8,249,311 B2 | 8/2012 | Endo et al. | |
| 8,258,968 B2 | 9/2012 | Ghazarian et al. | |
| 8,275,175 B2 | 9/2012 | Baltatu et al. | |
| 8,280,436 B2 | 10/2012 | Harris, Jr. | |
| 8,317,697 B2 | 11/2012 | Hawthorne et al. | |
| 8,326,001 B2 | 12/2012 | Free | |
| 8,331,632 B1 | 12/2012 | Mohanty et al. | |
| 8,340,366 B2 | 12/2012 | Masuda et al. | |
| 8,358,811 B2 | 1/2013 | Adams et al. | |
| 8,359,901 B2 | 1/2013 | Freund et al. | |
| 8,369,891 B2 | 2/2013 | Harris, Jr. | |
| 8,373,753 B2 | 2/2013 | Cheng et al. | |
| 8,379,940 B2 | 2/2013 | Wechsler et al. | |
| 8,381,573 B2 | 2/2013 | Keays | |
| 8,392,957 B2 | 3/2013 | Holt et al. | |
| 8,396,265 B1 | 3/2013 | Ross et al. | |
| 8,406,525 B2 | 3/2013 | Ma et al. | |
| 8,416,997 B2 | 4/2013 | Winters et al. | |
| 8,442,279 B2 | 5/2013 | Yan et al. | |
| 8,548,257 B2 | 10/2013 | Reid et al. | |
| 8,553,947 B2 | 10/2013 | Benini | |
| 8,559,681 B2 | 10/2013 | Benini | |
| 8,666,122 B2 | 3/2014 | Yan et al. | |
| 8,707,758 B2 | 4/2014 | Keays | |
| 2002/0097145 A1* | 7/2002 | Tumey | B60R 25/04 340/426.28 |
| 2002/0127145 A1 | 9/2002 | Der Ghazarian et al. | |
| 2003/0204290 A1* | 10/2003 | Sadler | B60R 25/04 701/1 |
| 2006/0202837 A1 | 9/2006 | Hawthorne et al. | |
| 2007/0144812 A1* | 6/2007 | Stewart | B60K 28/063 180/272 |
| 2007/0239992 A1 | 10/2007 | White et al. | |
| 2008/0183502 A1 | 7/2008 | Dicks et al. | |
| 2008/0314115 A1 | 12/2008 | Faulder et al. | |
| 2009/0060293 A1 | 3/2009 | Nagao et al. | |
| 2009/0169068 A1 | 7/2009 | Okamoto | |
| 2009/0325639 A1 | 12/2009 | Koehn | |
| 2010/0010689 A1 | 1/2010 | Yasushi | |
| 2010/0028210 A1* | 2/2010 | Ozaki | B60K 28/063 422/84 |
| 2010/0108425 A1 | 5/2010 | Crespo et al. | |
| 2010/0204600 A1 | 8/2010 | Crucilla | |
| 2010/0251804 A1 | 10/2010 | Morley et al. | |
| 2011/0299741 A1 | 12/2011 | Zhang | |
| 2011/0309932 A1* | 12/2011 | Arringdale | B60K 28/063 340/539.14 |
| 2012/0021153 A1 | 1/2012 | Bhandari et al. | |
| 2012/0031166 A1 | 2/2012 | Lopez et al. | |
| 2012/0075094 A1 | 3/2012 | Keays | |
| 2012/0075462 A1 | 3/2012 | Chen et al. | |
| 2012/0102332 A1* | 4/2012 | Mullin | G06F 1/1626 713/186 |
| 2012/0112879 A1 | 5/2012 | Ekchian | |
| 2012/0174651 A1 | 7/2012 | Mitchell | |
| 2012/0188532 A1 | 7/2012 | Li et al. | |
| 2013/0021153 A1* | 1/2013 | Keays | G01N 33/4972 340/539.12 |
| 2013/0035602 A1* | 2/2013 | Gemer | A61B 5/0404 600/484 |
| 2013/0245483 A1 | 9/2013 | Eichler | |
| 2014/0187993 A1 | 7/2014 | Contestabile et al. | |
| 2014/0311215 A1 | 10/2014 | Keays et al. | |
| 2014/0320285 A1 | 10/2014 | Keays et al. | |
| 2014/0335905 A1 | 11/2014 | Bhoot | |
| 2015/0084774 A1 | 3/2015 | Wojcik et al. | |
| 2016/0358029 A1* | 12/2016 | Mullin | G06K 9/00892 |

OTHER PUBLICATIONS

"MEMS 2000: Reliable Alcohol Monitoring System Incorporating Fully Integrated Home Detention Monitoring Capabilities," Sadna, Feb. 2002, 2 pages.
"MEMS 3000 Homestation Installation Guide," Elmo tech Ltd., Mar. 2006, 21 pages.
International Search Report and Written Opinion for International (PCT) Patent Application No. PCT/US14/52465, dated Jan. 27, 2015, 15 pages.
Office Action Non-Final for U.S. Appl. No. 14/038,448 Titled "Remote Breath Alcohol Monitor" Filed on Sep. 26, 2013, 57 pgs.
U.S. Appl. No. 14/038,448, filed Sep. 26, 2013, Final Office Action dated Apr. 19, 2016, Emily C. Terrell, ## pages.
U.S. Appl. No. 14/038,448, filed Sep. 26, 2013, Advisory Action dated Jul. 19, 2016, Emily C. Terrell, 3pages.
U.S. Appl. No. 14/038,448 Titled "Remote Breath Alcohol Monitor" filed Sep. 26, 2013 Final Office Action dated Mar. 7, 2017, 67 pages.
U.S. Appl. No. 14/038,448, filed Sep. 26, 2013, Non-Final Office Action dated Jan. 17, 2017, Emily C. Terrell, 55 pages.
Hyung-Keun Jee et al.; Liveness Detection for Embedded Face recognition System; Jan. 1, 2008; World Academy of Science, Engineering and Technology; pp. 941-944.
Kraus, Leonie; Extended European Search Report (Supplementary European Search Report and European Search Opinion); European Patent Office; dated Apr. 3, 2017.
U.S. Appl. No. 14/038,448, filed Sep. 26, 2013, Non-Final Office Action dated Sep. 29, 2017, Emily C. Terrell, 60 pages.

* cited by examiner

REMOTE BREATH ALCOHOL MONITOR

CROSS-REFERENCES TO RELATED APPLICATIONS

This application is a continuation-in-part of application Ser. No. 14/038,448 filed on Sep. 26, 2013 titled "Remote Breath Alcohol Monitor" which is incorporated herein by reference in its entirety for all that is taught and disclosed therein.

BACKGROUND

This application relates to the technical field of breath alcohol monitoring, and more particularly to a portable handheld wireless breath alcohol monitoring device that utilizes facial recognition and automatic retesting if an initial test is positive for alcohol or if an initial facial match is negative.

When an offender is convicted of DUI, domestic violence, or another alcohol-related offense, a typical condition of sentencing or probation is that the individual must stop drinking for a specified period of time. To enforce this prohibition, courts have traditionally looked to random testing methods (blood, breath, ethyl glucuronide or EtG) that only showed if the individual was sober at the specific "point in time" the test was administered. Requiring sobriety of substance-involved offenders under correctional supervision has been trending since the 1980s, when the first Drug Court was established in Miami-Dade County, Fla. Over the next twenty-five years, enforcing sobriety for drug offenders became standard operating procedure in programs throughout the country. Random drug testing became the cornerstone of these treatment-focused courts. The overall philosophy of jurisprudence shifted to a focus on treating the addiction and utilizing swift interventions and sanctions for violations.

Alcohol, however, has proven to be more complex than drugs for the courts to manage. Despite the emphasis on drug abuse, alcohol remains the number one drug of abuse in the U.S. corrections system. In fact, it is widely reported that once drug offenders begin random drug testing, they often switch to alcohol as their drug of choice because alcohol may be legally purchased and with standard, random testing the offender can begin drinking right after a test and sober up before the next test.

While drug testing, which is usually done on a random schedule, is relatively accurate and cost-effective, the metabolism of the human body makes monitoring for alcohol far more complex. Alcohol is metabolized in the liver, which eliminates 95-98% of ingested alcohol from the body. No matter the rate of ingestion, it can only be metabolized at a certain rate, which can vary from person to person. A small amount of alcohol, about 1-5%, avoids metabolism in the liver and is excreted, unchanged, through the kidneys (urine), the lungs (breath), or the skin (perspiration).

Healthy people, on average, metabolize alcohol at a fairly consistent rate: one standard drink (or 0.5 ounces of alcohol) per hour. Heavy alcohol users may metabolize alcohol at a significantly higher rate than average individuals.

The result is that it is not just possible, it is probable, that an individual can be tested in the early evening at 6:00 pm or 7:00 pm and then gets very intoxicated when they go to bed at 10:00 pm, yet be completely sober in less than eight hours for their next alcohol test. The more severe the alcohol dependence, the faster an individual may metabolize the alcohol and avoid detection between tests.

Breath, blood, and urine testing are all reliable at testing individuals for alcohol consumption at any given "point in time." In 2003 transdermal alcohol testing was introduced as a way to test offenders for alcohol, without requiring active participation of the offender, and at a frequency rate high enough to ensure the offender stayed sober all day long. Typically, for transdermal alcohol testing, an ankle bracelet is attached to the offender with a durable and tamper-proof strap. The ankle bracelet is worn 24/7 by the offender for the duration of his or her court-ordered abstinence period. Periodically, such as every half-hour or hour, the bracelet analyzes samples of the insensible perspiration coming off the offender's skin and generates transdermal alcohol readings. The bracelet stores this data and, at pre-determined times, transmits the data to a base station or a monitoring network where the data can be analyzed. The testing protocol is prescheduled and automated, eliminating the offender's ability to manipulate the testing schedule or avoid or delay a request to test. Transdermal analysis and continuous alcohol monitoring (CAM) weren't developed because conventional testing is unreliable. They were developed because offenders who misuse alcohol are unreliable.

Current testing options to enforce sobriety are available on a continuum, from incarceration—the most intense sanction and most costly per day—to ignition interlock, which when installed only tests for sobriety when someone is driving (see FIG. 1).

These testing options range in cost and vary in terms of behavioral risk. Employing an assessment process to determine how to balance supervision and monitoring costs with the risk level of each offender is essential to a successful alcohol testing and monitoring program. Lower risk offenders who misuse alcohol may be assigned a less intrusive and less expensive testing and monitoring approach. High risk offenders who are alcoholic dependent or addicted may be assigned a more intrusive, vigorous, and expensive testing and monitoring regimen. Upon successful performance over a several month period of time, high risk offenders may be rewarded for their good behavior by being transitioned to a more convenient, less intrusive, and less expensive testing and monitoring approach.

SUMMARY

This Summary is provided to introduce in a simplified form a selection of concepts that are further described below in the Detailed Description. This Summary is not intended to identify key or essential features of the claimed subject matter, nor is it intended to be used to limit the scope of the claimed subject matter.

The detailed description below describes a portable handheld wireless breath alcohol monitoring device that utilizes facial recognition and automatic retesting if an initial test is positive for alcohol or a negative facial match. In addition, a location fix is captured with each breath test. The solution described below enables the monitoring of lower-risk offenders or offenders who have earned the privilege of a less intrusive alcohol testing and monitoring program.

The remote breath alcohol monitor (RBAM) described below is portable, easy to carry, and easy to use. It can be programmed with flexible testing schedules with multiple options for both the agencies that require the use of the device and for the offenders who are required to use the device. RBAM features an automated intelligent bio-confirmation system that utilizes facial recognition software that automatically matches an enrollment image or gallery of images of the offender with an image taken at the time of a breath test through a built-in high resolution camera, ensuring that the offender being monitored is the individual actually taking the breath test. The facial recognition software is also able to distinguish between a live person and a printed photograph or mask. Other image-based bio-confirmation methods could be adapted to perform the same function, such as iris recognition and cornea recognition. RBAM has built in wireless cellular communication and in one embodiment is GPS enabled to identify a location fix for each test. Other methods may be used to provide a location fix, including cell-tower triangulation, nearest cell site, other network-based or SIM-based methods commonly referred to as location-based services. Other methods being developed includes crowd sourced Wi-Fi data, Wi-Fi positioning systems, and IP-based geo-location methods. A location fix is captured when the schedule calls for a breath test even when the user fails to take a breath test, referred to as a missed test.

RBAM employs an ethanol fuel cell to determine breath alcohol content (BrAC) and can be programmed for a set schedule, a random schedule, a flexible schedule (each test can be completed within a predetermined span of time, such as one hour or three hours, etc.), or on-demand testing initiated by supervisory personnel. Other types of ethanol sensors that are not fuel cells may also be used, such as metal oxide sensors or proton exchange membranes. It is anticipated that technologies currently under development and future technologies, such as quartz microbalance (QMB) sensors and thin-film bulk acoustic resonator-based (FBAR) sensors technology, may provide still other types of sensors suitable for this purpose. A supervising agency can be immediately notified, or on a priority notification basis within a relatively short period of time, such as fifteen minutes, upon a positive breath test, negative facial match, or other criteria or combinations of criteria. A positive initial test is automatically followed by a retest, or confirmation test. A negative facial match may also be followed by a retest.

A unique aspect of the RBAM is its active supervision functionality. A schedule for testing, which can be distinct for each offender, is downloaded from a monitor network directly to the RBAM for the particular offender. Then, based on the schedule that has been downloaded, the RBAM wakes itself up when it is time for a scheduled test and prompts the offender to take a breath test. The RBAM does not need to be in communication with the monitor network to follow the downloaded test schedule. In addition, supervisory personnel can initiate an on-demand breath test at any time apart from the schedule (provided that there is a communication link available), and download the on-demand breath test request to the RBAM. The RBAM will wake up (turn itself on) upon receiving the on-demand test request and prompt the offender to take an unscheduled breath test.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xm, Y1-Yn, and Z1-Zo, the phrase is intended to refer to a single element selected from X, Y, and Z, a combination of elements selected from the same class (e.g., X1 and X2) as well as a combination of elements selected from two or more classes (e.g., Y1 and Z3).

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "means" as used herein shall be given its broadest possible interpretation in accordance with 35 U.S.C., §112, Paragraph 6. Accordingly, a claim incorporating the term "means" shall cover all structures, materials, or acts set forth herein, and all of the equivalents thereof. Further, the structures, materials or acts and the equivalents thereof, shall include all those described in the summary of the invention, brief description of the drawings, detailed description, abstract, and claims themselves.

"Lower Limit of Detection" (LLOD) means a user settable field that may be pulled down from a monitor network by the RBAM or programmed into the RBAM. In one embodiment the proposed range is from 0.020% to 0.050% BrAC in increments of 0.005%, with a default of 0.020%. One skilled in the art will recognize that other units of measure, ranges, increments, and defaults may be used to suit particular demands or purposes. Breath tests results are considered positive (see definition below) if they are ≥LLOD, and are considered negative (see definition below) if they are <LLOD.

"Valid Sample" means the offender properly blows into the RBAM and provides an adequate breath sample for analysis. All valid samples lead to either a positive or negative breath test result.

"Invalid Sample" means the offender does not properly blow into the RBAM and does not provide a valid breath sample for analysis. This is almost always because the offender did not blow long enough or hard enough. An invalid sample cannot produce a test result.

"No Sample" means the offender does not blow into the RBAM at all. A no sample cannot produce a breath test result.

"Initial Test" means the first test provided at a scheduled test time or an on-demand test. If the initial test is a negative test (see definition below), then it is the only test for that scheduled time or on-demand request.

"Missed Test" means that a test was scheduled or was an on-demand test, and the offender failed to take the test and never attempted to blow into the RBAM.

"Confirmation Test" or "Retest" means a second test taken shortly after an initial test that was a positive test (see definition below) or after a negative facial match. The confirmation test is intended to determine if the initial test was caused by actual deep-lung breath alcohol (and therefore blood alcohol), or by mouth alcohol. To allow time for mouth alcohol to dissipate, the confirmation test occurs after a certain Wait-To-Retest Period (see definition below) has passed. A confirmation test can also be performed after a negative facial match, allowing the offender to remove sunglasses or be given a second chance if they allowed a different person to take their test, for example.

"Retry" means that when there is an invalid sample, the offender is prompted to blow again in order to complete an initial test or a confirmation test. A retry should not be confused with a retest/confirmation test. A confirmation test can also be performed after a negative facial match, allowing the offender to remove sunglasses or be given a second chance if they allowed a different person to take their test, as examples.

"On-Demand Test" means a breath test that occurs outside of the defined test schedule. Personnel from a supervising agency may request an on-demand test through a web interface to a monitoring network. When the RBAM checks in to the monitoring network, the on-demand request is downloaded to the RBAM and the RBAM will power on and prompt the offender to take a breath test.

"Negative Test" means a test where the offender provides a valid sample, and the breath test result or BrAC is less than the LLOD set by the user.

"Positive Test" means a test where the offender provides a valid sample, and the BrAC result of that sample is greater than or equal to the LLOD set by the user. Positive tests can be caused by either actual deep-lung breath alcohol (and therefore blood alcohol), or by mouth alcohol. Therefore, in one embodiment, a confirmation test may be required for all initial positive tests.

"Grace Period" means the time allowed from when the breath test is supposed to be performed to when the offender must start blowing. E.g., if the grace period is ten minutes, an offender can start blowing for a 10:00 AM test as late as 10:10 AM. This is a user selectable variable that may be pulled down from a monitor network by the RBAM or programmed into the RBAM. In one embodiment the proposed range is from two to sixty minutes in increments of one minute, with a default of fifteen minutes. Note that the grace period does not apply to confirmation tests/retests.

"Wait-To-Retest Period" means the time after an initial test that the offender must wait to provide a confirmation test. This is a user selectable variable that may be pulled down from a monitor network by the RBAM or programmed into the RBAM. The wait-to-retest period can be no shorter than the recovery period (see definition below). In one embodiment the proposed range is from two to twenty minutes in increments of one minute, with a default of two minutes.

"Recovery Period" means the minimum time after a valid sample that the offender must wait before providing another breath sample and is hardware driven. E.g., if the fuel cell, and sample system require 83 seconds to "recover," the recovery period must be greater than 83 seconds and could be rounded to 90 or 120 seconds. The recovery period defines the minimum allowable wait-to-retest period.

"Initial Testing Window" means how long the offender has after the RBAM prompts the offender to "BLOW" to provide a valid sample, including all retries. When the initial testing window expires the RBAM locks until the next scheduled test or on-demand test. In one embodiment, the initial testing window is set for five minutes. The initial testing window does not have to be time-based, but could also be determined by limiting the number of retry attempts, or by some combination of time and retry attempts. In another embodiment, the RBAM may be allowed to stay powered up and not locked to allow for a breath test outside of the initial testing window.

"Confirmation Testing Window" is analogous to the initial testing window, but applies to confirmation tests/retests. After the wait-to-retest period has expired, the RBAM will display "Blow" for the confirmation test, and the offender has to provide a valid sample before the confirmation test window expires, including all retries. If the offender does not, then a missed test or incomplete confirmation test will be reported. In one embodiment, the confirmation testing window is set for five minutes. The confirmation testing window does not have to be time-based, but could also be determined by limiting the number of retry attempts, or by some combination of time and retry attempts. In another embodiment, the RBAM may be allowed to stay powered up and not locked to allow for a breath test outside of the confirmation testing window.

The testing windows above in one embodiment are configurable variables, but not user selectable. They may be pulled down from a monitor network by the RBAM as part of a configuration file, enabling the option to change them system-wide if needed. For example, if some field experience indicates that the confirmation test window is too long or short, one change can be made to the configuration file and this new change will make its way down to each RBAM over time.

"Circumvention Detected" means any test in which the person blowing into the RBAM is identified not to be the offender, or in which the offender is attempting to provide the breath sample from a source other than the offender's own breath. In both situations, in one embodiment, this determination is made through inspection of the test image (s) or comparison of the test image(s) to a comparison image or a gallery of images, either manually or via an automated method. In one embodiment, prior to being confirmed as an attempted circumvention detected, test results are labeled as Pending Review.

"Test Results" means one or more of breath tests, location fixes, facial match results, match scores, quality scores, templates, and images of the offender taken with the remote breath alcohol monitor.

Figure 1:
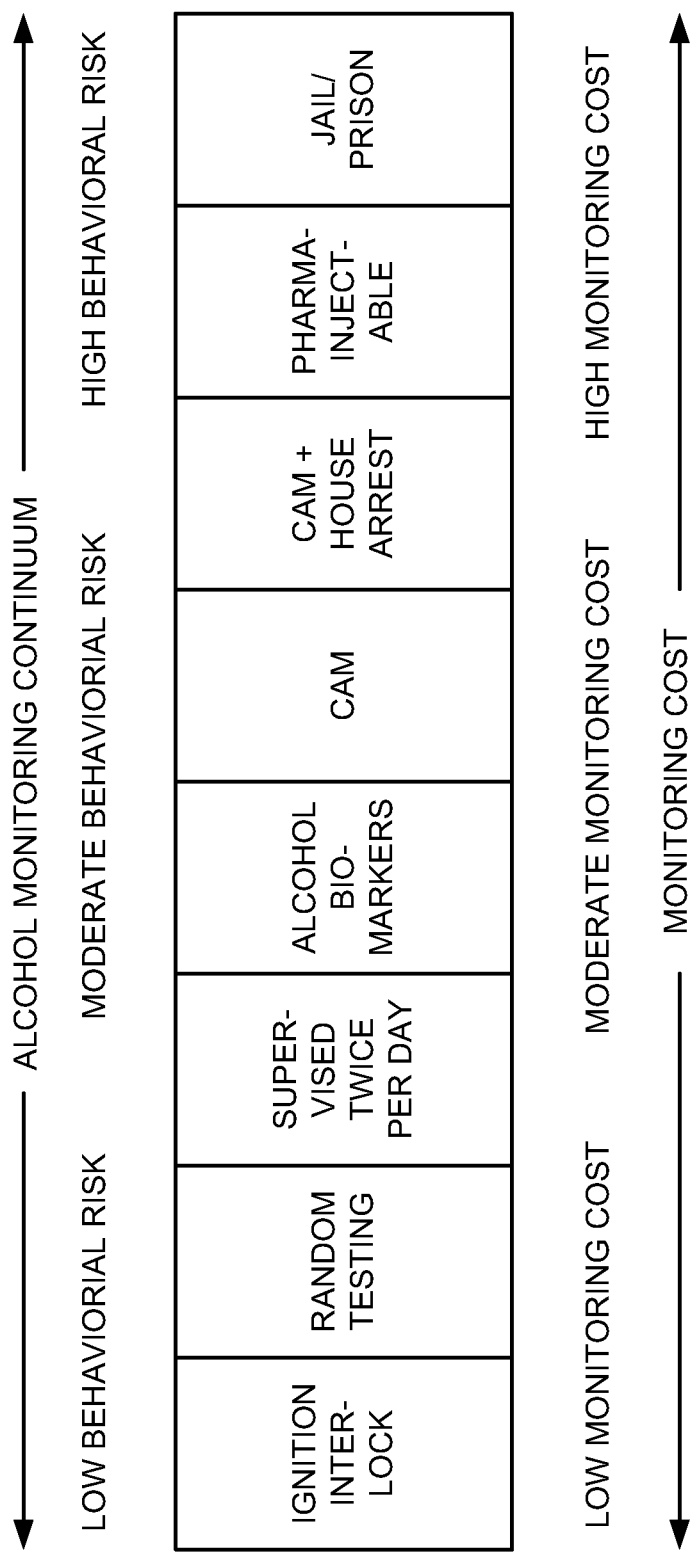
FIG. 1 shows a chart of the alcohol monitoring continuum ranging from low risk/low cost to high risk/high cost.

To assist in the understanding of the present disclosure the following list of components and associated numbering found in the drawings is provided herein:

TABLE OF COMPONENTS

| Component | # |
|---|---|
| Housing Front Panel | 1 |
| Housing Back Panel | 2 |
| Housing Battery Door | 3 |
| Window Assembly | 4 |
| Switch/Indicator Panel | 5 |
| Battery Pack | 6 |
| Main Circuit Board Assembly | 7 |
| Processor Circuit Board Assembly | 8 |
| Camera Circuit Board Assembly | 9 |
| Fuel Cell Assembly With Tubing | 10 |
| OLED Display | 11 |
| Pump | 12 |
| RF Shield | 13 |
| Breath Tube | 14 |
| USB and Ethernet Connector | 15 |
| Charging Connection | 16 |
| Mirrors | 17 |
| Camera | 18 |
| Mute Switch | 19 |
| Visual Speaker Indicator | 20 |
| Power On/Off Switch | 21 |
| Battery Indicator | 22 |
| Visual Battery Indicator | 23 |
| Speaker | 24 |
| Vent Opening | 25 |
| Connectors | 26 |
| Opening | 27 |
| Remote Breath Alcohol Monitor (RBAM) | 200 |
| Offender | 202 |
| Cellular Network | 204 |
| Ethernet | 205 |
| Monitor Network | 206 |
| Monitoring Station | 208 |
| Supervising Agency | 210 |
| Wireless Communication Link | 212 |
| Ethernet Communication Link | 213 |
| Communication Link | 214 |
| Ethernet Communication Link | 215 |
| Internet | 216 |
| Communication Link | 218 |
| Internet Connection | 220 |
| Communication Link | 222 |
| Method | 300 |
| Initial Test Routine | 315 |
| Initial Retry Test Subroutine | 329 |
| Confirmation Test Routine | 353 |
| Confirmation Retry Test Subroutine | 367 |
| Messages | 602 |
| Time of Day | 604 |
| Cellular Signal Strength | 606 |
| Battery Strength | 608 |

DETAILED DESCRIPTION

Referring now to the figures, like reference numerals and names refer to structurally and/or functionally similar elements thereof, and if objects depicted in the figures that are covered by another object, as well as the tag line for the element number thereto, may be shown in dashed lines. FIG. 1 shows a chart of the alcohol monitoring continuum ranging from low behavioral risk/low monitoring cost to high behavioral risk/high monitoring cost. Referring now to FIG. 1 and moving from left to right, low risk offenders may be required to have an ignition interlock device or breath alcohol ignition interlock device (IID and BAIID) installed on their vehicle. An IID or BAIID is a mechanism, like a breathalyzer, installed on a motor vehicle's dashboard. Before the vehicle's engine can be started, the driver first must exhale into the device. If the resultant BrAC is greater than the programmed BrAC (which varies between jurisdictions), the device prevents the engine from being started.

Next on the continuum is a random testing program. Typical programs require the offender to submit to random alcohol and drug screens on the days they appear for their status hearings and random days between court appearances and in some cases unannounced home visits by a probation officer.

A more rigorous testing program on the alcohol monitoring continuum has an abstinence requirement and requires an offender to report to a local sheriff's office or other designated location twice daily for alcohol testing. Typical times are between 7 a.m. and 9 a.m. and between 7 p.m. and 9 p.m.

Next on the continuum is the use of alcohol biomarkers, which are physiological indicators of alcohol exposure or ingestion. Alcohol biomarkers are generally divided into indirect and direct biomarkers. Indirect alcohol biomarkers suggest heavy alcohol use by detecting the toxic effects that alcohol may have had on organ systems or body chemistry. Direct alcohol biomarkers are analytes of alcohol metabolism. Direct alcohol biomarkers include alcohol itself and ethyl glucuronide (EtG).

Continuous alcohol monitoring (CAM) is next on the alcohol monitoring continuum scale. CAM is accomplished with a transdermal alcohol monitoring device that is worn on the body of the offender. One such device is the Secure Continuous Remote Alcohol Monitor, or SCRAM®, from Alcohol Monitoring Systems, Inc., Littleton, Colo. Transdermal alcohol monitoring means that alcohol is measured "through the skin," or by the content of alcohol present in the insensible perspiration that is constantly given off by the skin. If an offender has been drinking, it shows up in the level of ethanol vapor present in this insensible perspiration.

Next on the continuum is the use of CAM combined with house arrest. House arrest (also called home arrest, home confinement, home detention, curfew monitoring, or electronic monitoring) is a measure by which a person is confined by the authorities to a certain residence. Travel is usually restricted, if allowed at all. House arrest is a lenient alternative to prison time. House arrest is often enforced through the use of technology devices or services. One method is an electronic sensor locked to the offender's ankle (technically called an ankle monitor, and sometimes referred to as a tether). Typically, the electronic sensor transmits a radio frequency signal to a fixed base station. The base station is connected to a police facility or a monitoring service. Most programs allow employed offenders to continue to work, and only confine them to their house during non-working hours. House arrest can also be accomplished with GPS tracking bracelets. Some devices combine CAM with house arrest tracking in a single device, such as SCRAM® from Alcohol Monitoring Systems, Inc., Littleton, Colo. Other existing devices combine CAM with GPS tracking.

Next, pharma-injectible drugs may be used for some high behavioral risk offenders. After being injected, if the offender drinks alcohol, these drugs produce a physical reaction that may include flushing, nausea, vomiting, and headaches.

Finally on the alcohol monitoring continuum scale, jail or prison may be the only option for the highest behavioral risk offenders. This option is also the most expensive.

The use of RBAM 200 (see FIG. 2) that is the subject of this disclosure is positioned toward the low behavior risk and low monitoring cost on the alcohol monitoring continuum. The typical candidate for RBAM 200 would be a first time or second time DUI offender or one who has committed a public order offense. The offender would typically have a low blood alcohol content (BAC) or BrAC at the time of arrest. For those offenders who start out on a higher risk/higher cost alternative, their compliance with those standards would allow them to earn the right to this lower cost and less intrusive alcohol monitoring solution.

Figure 2:
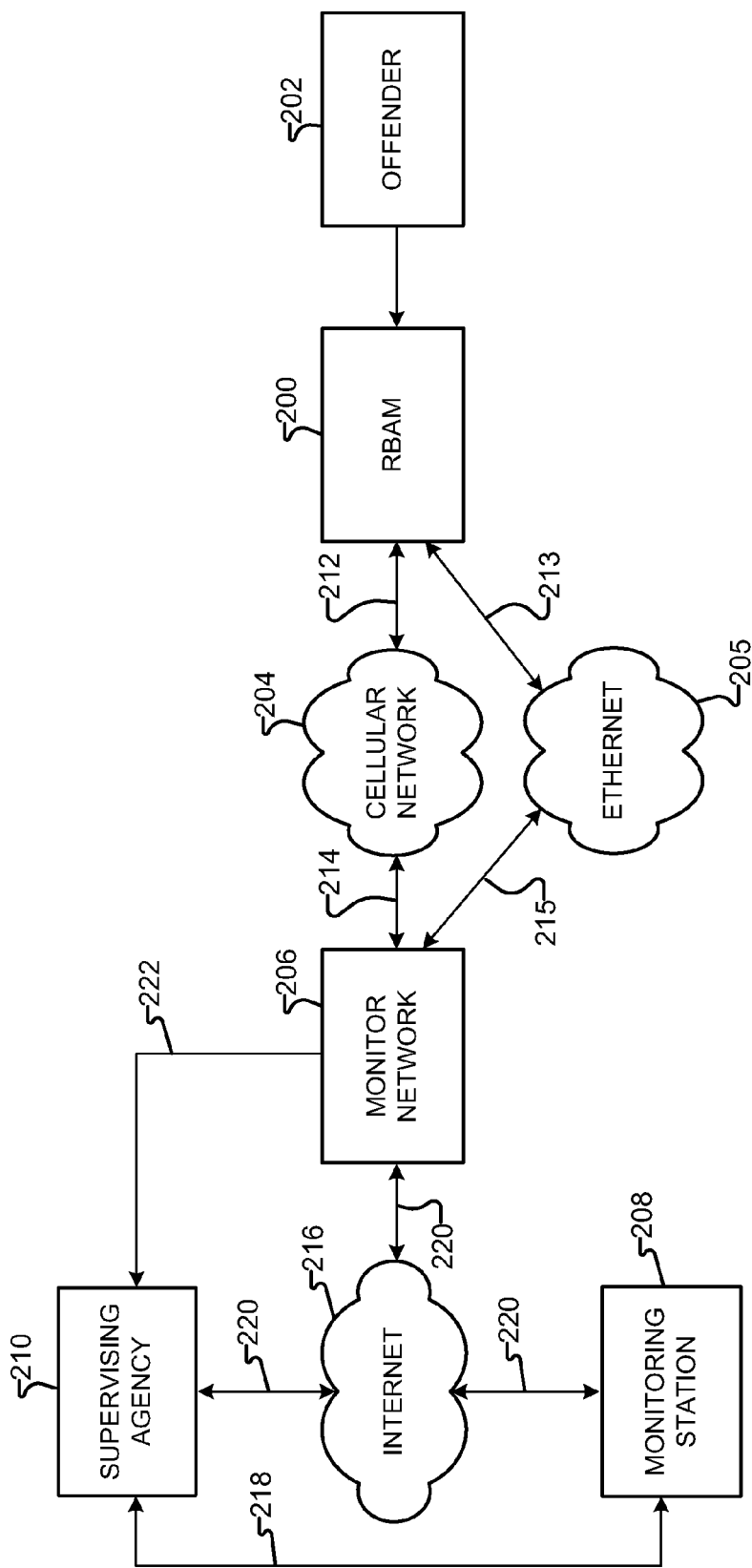
FIG. 2 shows a schematic/block diagram of an overall system in an embodiment of the remote breath alcohol monitor.

FIG. 2 shows a schematic/block diagram of the overall system of an embodiment of remote breath alcohol monitoring. Referring now to FIG. 2, in one embodiment RBAM 200 is a portable handheld wireless breath alcohol tester with built in cellular, GPS, and facial recognition capabilities that is designed to be rugged for everyday use in the corrections environment. The facial recognition software is available from multiple third party vendors, such as Omron Corporation of Tokyo, Japan, Animetrics, Inc. of Conway, N.H., or Fulcrum Biometrics, LLC, of San Antonio, Tex. For different applications, design criteria, and cost considerations, one of the products from one of these, or other vendors, may be more suitable. RBAM 200 is used by the Offender 202 being monitored in a manner to be described below. RBAM 200 can be carried around by Offender 202 throughout the day and night, just like a typical cell phone. There are a number of anti-tamper features designed into RBAM 200 to ensure that the breath tests taken are from Offender 202, and accurately represent the breath alcohol level of Offender 202 and not some other person. Though this discussion focuses on one Offender 202, one skilled in the art will recognize that many RBAM 200s may be used by many Offender 202s at the same time over a broad geographic area, and all may be monitored by Monitor Network 206, which is the intended purpose. Likewise, there may be multiple Monitor Networks 206 and Monitoring Stations 208 that manage additional Offender 202s in diverse geographic locations.

Offender 202 will be instructed by RBAM 200 to provide breath tests that are time stamped at scheduled or random intervals during any given twenty-four hour period, and could be seven days a week, 365 days a year, or any given set of days. There may be days when no tests are required. Testing schedules may vary from one Offender 202 to another Offender 202. Offender 202 typically knows when the request to give fixed breath tests will occur. Random monitoring eliminates the ability for Offender 202 to manipulate drinking patterns to avoid detection. Offender 202 typically does not know when the request to take random breath tests will occur.

Breath tests taken as scheduled, or randomly, are uploaded at the conclusion of each breath test along with the location fix, facial match results, and an image of Offender 202 taken while blowing. One or more of these are collectively referred to as test results. In other embodiments, only some of the test results may be uploaded based upon design requirements or other criteria. RBAM 200 places a call via Wireless Communication Link 212 to Cellular Network 204. Cellular Network 204 completes the call via Communication Link 214 to Monitor Network 206. In practice, Cellular Network 204 may actually be many different networks, including the Internet, interoperating with each other but is shown as a single network for simplicity. Communication Link 214 may be a wireless link or a combination of a wireless and a wired link.

In situations where there is very poor or nonexistent cellular coverage, RBAM 200 is provisioned for Ethernet communication. Offender 202 can simply plug RBAM 200 via USB and Ethernet Connector 15 into an Ethernet jack to connect to Ethernet 205 to Monitor Network 206.

If there is no Wireless Communication Link 212 or Ethernet 205 at the location where the breath test was taken, RBAM 200 will store the test results and send the test results when a Wireless Communication Link 212 becomes available. Once a Wireless Communication Link 212 is established, RBAM 200 calls Monitor Network 206 via Cellular Network 204 and Communication Link 214. Monitor Network 206 validates the identity of RBAM 200 and authenticates the test results before it is permanently stored. Monitor Network 206 then analyzes the test results received and separates and groups the test results into a number of separate categories for reporting to monitoring personnel at Monitoring Station 208. The test results can then be accessed by the monitoring personnel through the use of secured dedicated websites through the Internet 216 and Internet Connection 220 to Monitor Network 206. When Monitor Network 206 analyzes the test results received, an automatic alert, based upon predetermined, stored rules, may be sent directly from Monitor Network 206 to a call center at Supervising Agency 210 over Communication Link 222, or to an individual previously designated by Supervising Agency 210, when a specific alert, or combination of alerts, are received. The alert may be an e-mail, text message, or a page to a previously provided number. Communication Link 222 may be a wire or wireless connection. The term "server" used with respect to Monitor Network 206 may be one hardware device partitioned into many functional virtual servers, such as a central server, database server, rules-based server, etc., or it may be several hardware devices dedicated to a particular function, each in communication with each other.

Monitoring Station 208 may be located at Monitor Network 206, or in a separate location as shown in FIG. 2. Monitoring personnel at Monitoring Station 208 have access to all of the data gathered on all of the Offenders 202. Supervising personnel at the call center of Supervising Agency 210, however, only have access to those Offender 202s that are associated with Supervising Agency 210.

Monitoring Station 208 may automatically or periodically transmit data received from RBAM 200 via Cellular Network 204 to Monitor Network 206 to one or more persons at Supervising Agency 210 who are assigned to monitor Offender 202, such as a parole officer, probation officer, case worker, or other designated person or persons in charge of enrolling Offender 202 and monitoring the data being collected on Offender 202. Only one Supervising Agency 210 is shown for simplicity, but one skilled in the art will recognize that many Supervising Agencies 210 may be accessing Monitor Network 206 at any given time. A connection is established with Supervising Agency 210 through Communication Link 218. Typically this connection is accomplished via the telephone system through a wire or wireless link, and may connect to a pager or cellular phone of the designated person or via email. Designated personnel at Supervising Agency 210 may also access Monitor Network 206 through the use of secured dedicated websites through the Internet 216 and Internet Connection 220 to Monitor Network 206. Monitor Network 206 hosts a website that allows Supervising Agency 210 the ability to log on and track Offender 202 compliance in a manner most suitable to the needs of Supervising Agency 210, and can be defined to fit the needs of both small and large programs. Each Supervising Agency 210 may customize the frequency of testing and the method of notification for alerts that they want to receive from Monitor Network 206. Alerts may be categorized by the type and severity of alert, allowing each Supervising Agency 210 to prioritize and better categorize a response (e.g., a low battery warning versus a possible alcohol consumption violation).

Each Supervising Agency 210 has its own separate data storage area on the database server at Monitor Network 206 so that representatives from each Supervising Agency 210 can retrieve the secure data they need when they need it.

Figure 3A:
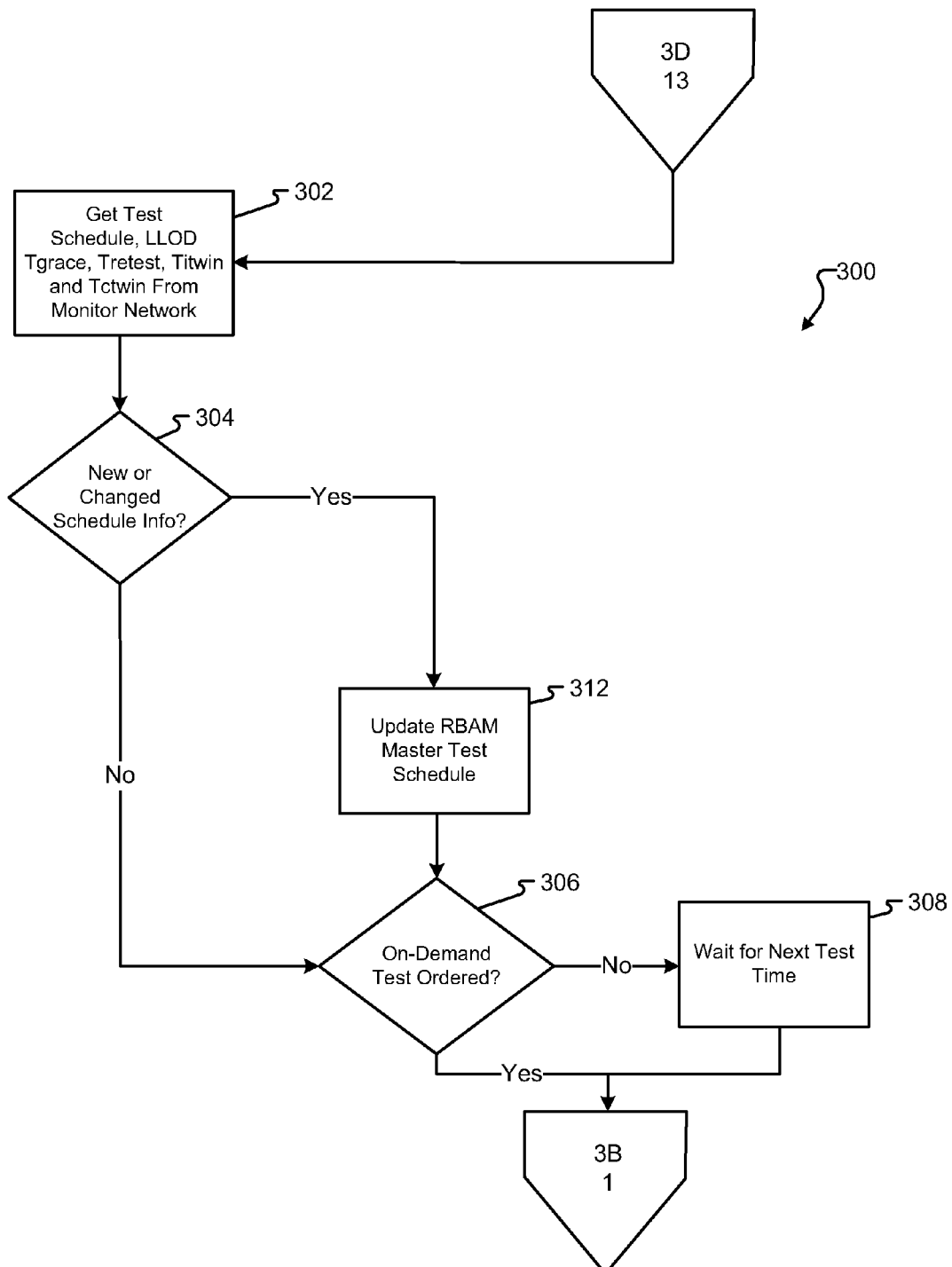
FIGS. 3A-3D show a flow chart of a general method from the offender's perspective of an embodiment of remote breath alcohol monitoring.

FIGS. 3A-3D show a flow chart of a general method from the offender's perspective of an embodiment of remote breath alcohol monitoring. Referring now to FIG. 3A, Method 300 begins in block 302 where an RBAM 200 assigned to a particular Offender 202 obtains the testing schedule, the Lower Limit of Detection (LLOD), the grace period designated as $T_{grace}$, the wait-to-retest period designated as $T_{retest}$, the initial testing window designated as $T_{itwin}$, and the confirmation testing window designated as $T_{ctwin}$, for this particular Offender 202 from Monitor Network 206. Decision block 304 determines if there is a new testing schedule or a changed testing schedule from what was previously stored in RBAM 200. If no, then decision block 306 determines if an on-demand test has been ordered. If no, then RBAM 200 in block 308 waits for the next scheduled test time from the RBAM master test schedule to arrive.

If the answer in decision block 304 is yes, then in block 312 the RBAM master test schedule in RBAM 200 is updated and stored in RBAM 200. If the answer in decision block 306 is yes, or, the next scheduled test time has arrived in block 308, control passes to block 316 in FIG. 3B.

Figure 3B:
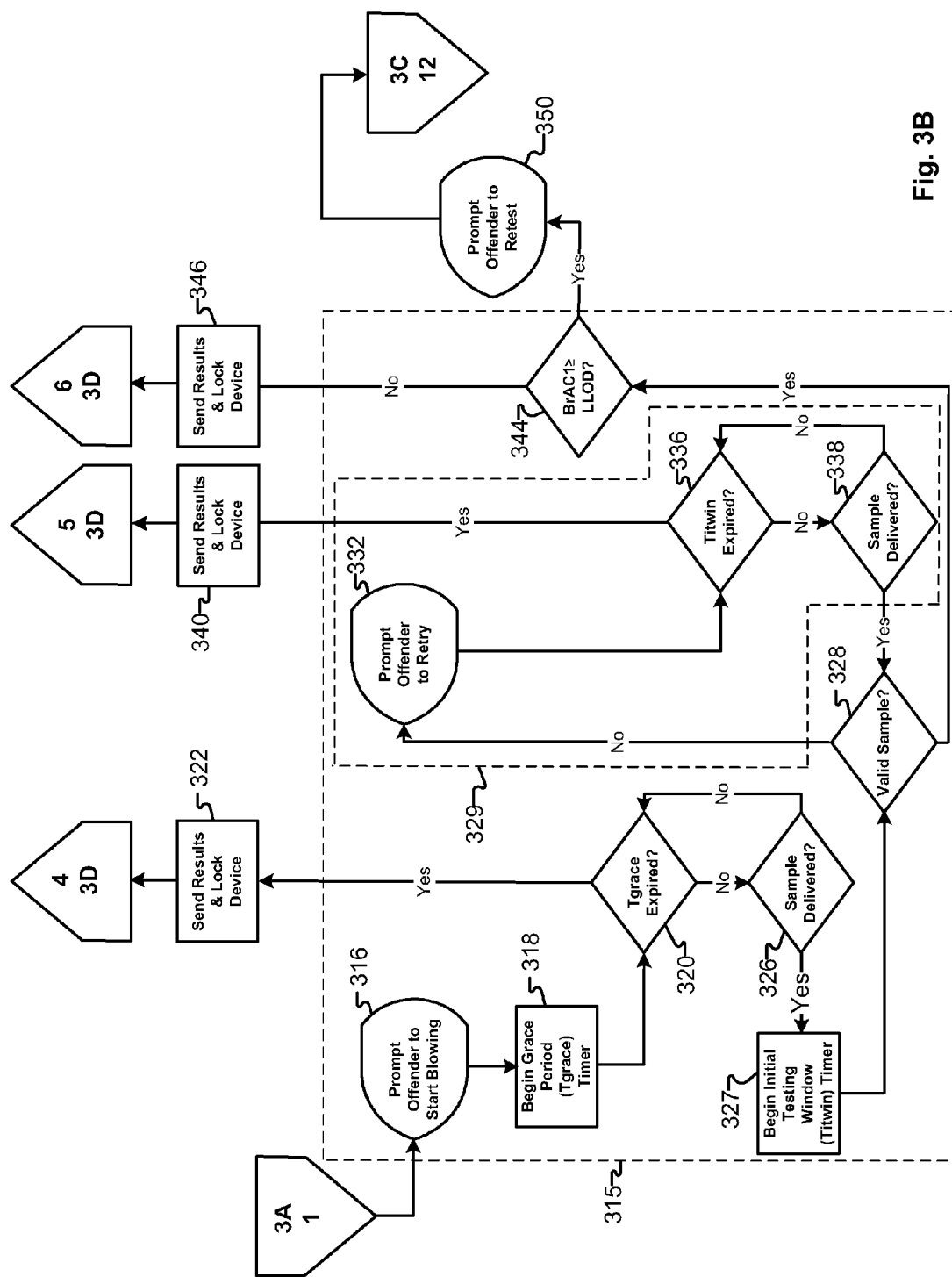

Referring now to FIG. 3B, the steps enclosed within Dashed Line Box 315 encompass the Initial Test Routine. In block 316 a message is displayed to Offender 202 on OLED Display 11 (see FIGS. 5B and 5C) such as "BLOW" which indicates that Offender 202 should insert Breath Tube 14 into RBAM 200 and begin blowing into Breath Tube 14. In block 318 the timer for the grace period ($T_{grace}$) is started. Decision block 320 determines if $T_{grace}$ has expired. If yes, this test result is sent to Monitor Network 206 in block 322 and RBAM 200 is locked, and control passes to block 324 in FIG. 3D.

Figure 3C:
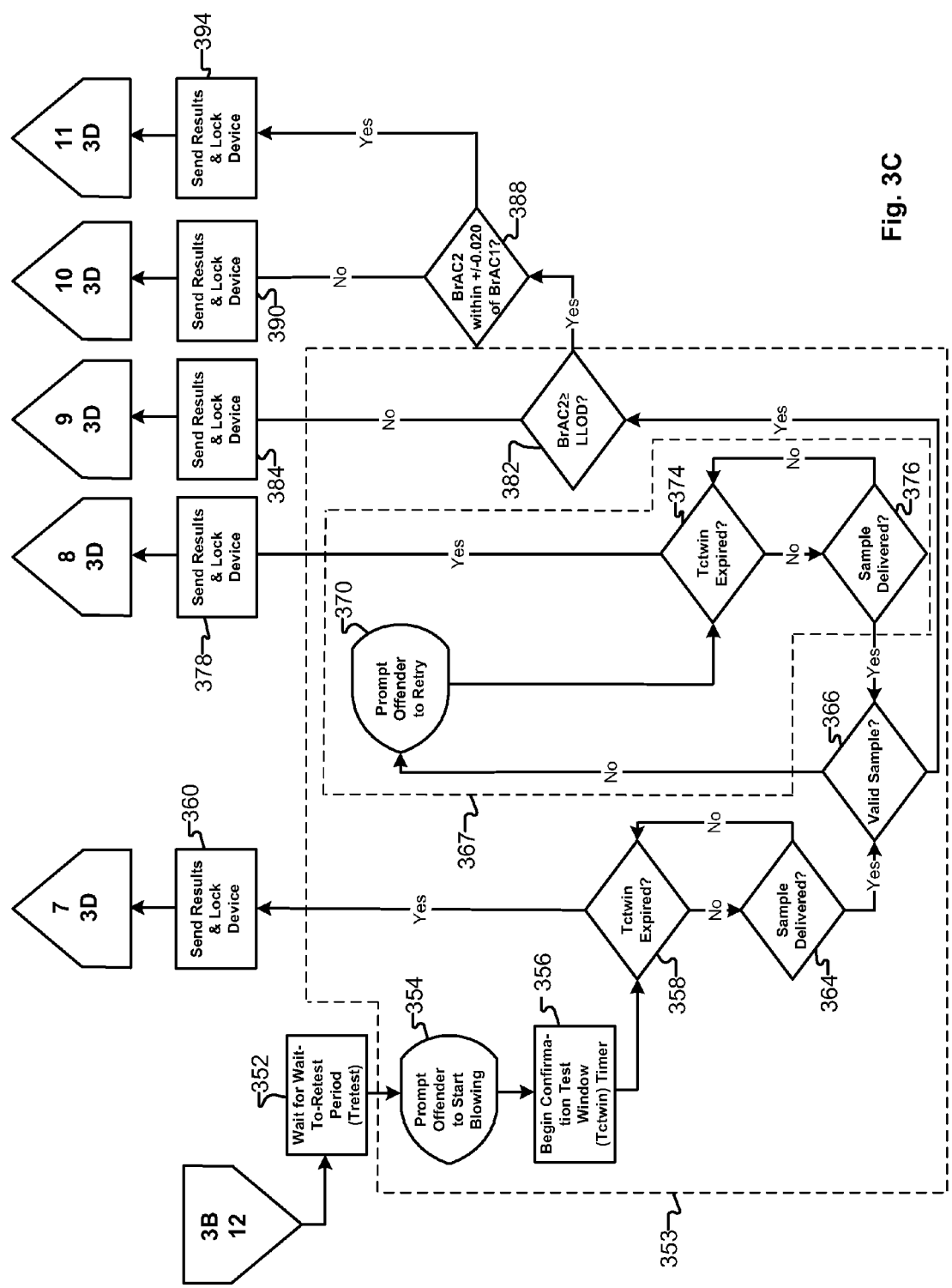
Figure 3D:
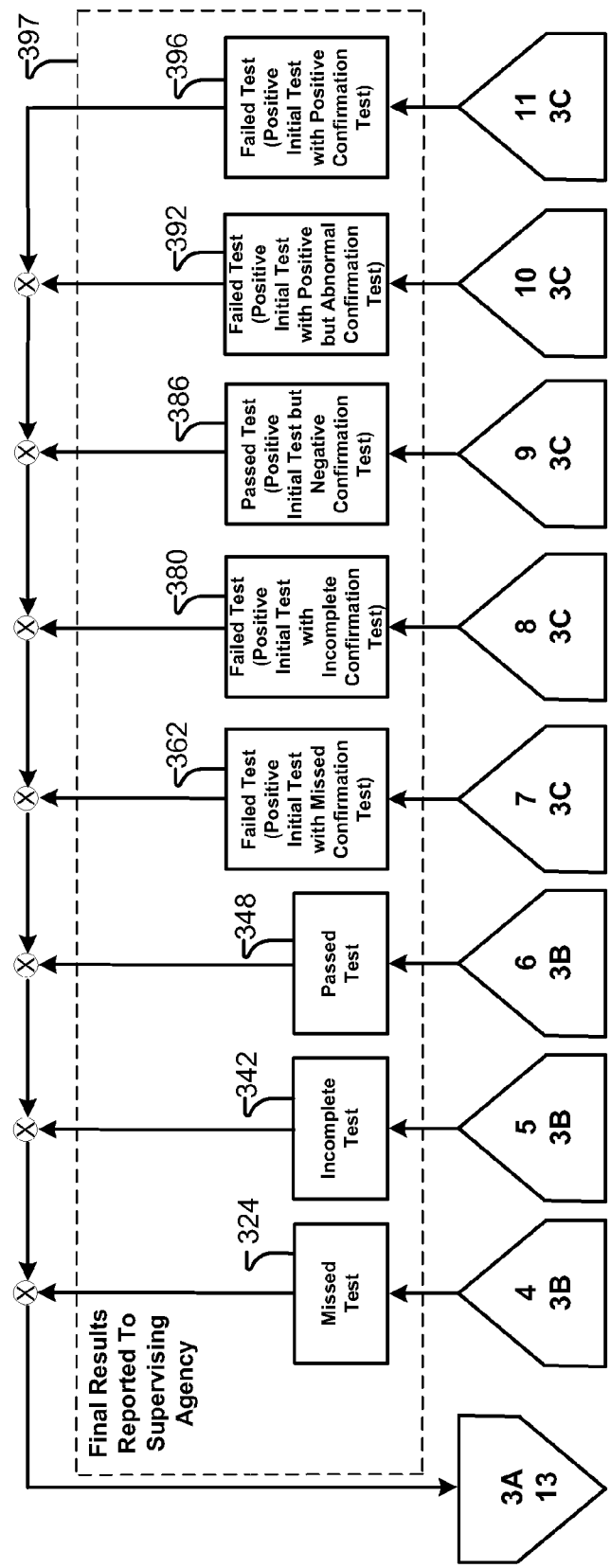

Referring now to FIG. 3D, in block 324 Monitor Network 206 sends a message to Supervising Agency 210 that a test was missed by Offender 202 if missed tests have been selected for immediate notification. The test results are stored in a server in Monitor Network 206. Control then returns to block 302 in FIG. 3A.

Referring back now to FIG. 3B, if decision block 320 determines that $T_{grace}$ has not expired, then decision block 326 determines if a breath sample has been delivered by Offender 202 into RBAM 200. If no, then control returns to decision block 320 to determine if $T_{grace}$ has expired. If decision block 326 determines that a breath sample has been delivered by Offender 202 into RBAM 200, then in block 327 the timer for the initial testing window ($T_{itwin}$) is started. Decision block 328 determines if the breath sample is a valid sample. If no, then control passes to the steps within Dashed Line Box 329 encompassing the Retry Subroutine. In block 332 a message is displayed to Offender 202 on OLED Display 11 asking Offender 202 to retry taking a breath test. Decision block 336 determines if $T_{itwin}$ has expired. If no, decision block 338 determines if a breath sample has been delivered. If yes, control returns to decision block 328 to determine if the breath sample is valid. If decision block 338 determines that no breath sample has been delivered, control returns to decision block 336 which determines if $T_{itwin}$ has expired. If no, control returns to decision block 338 to determine if a breath sample has been delivered. If $T_{itwin}$ has expired in decision block 336, this test result is sent to Monitor Network 206 in block 340 and RBAM 200 is locked, and control passes to block 342 in FIG. 3D.

Referring now to FIG. 3D, in block 342 Monitor Network 206 sends a message to Supervising Agency 210 that an incomplete test has occurred for Offender 202 if incomplete tests have been selected for immediate notification. The test results are stored in a server in Monitor Network 206. Control then returns to block 302 in FIG. 3A.

Referring back now to FIG. 3B, if decision block 328 determines that a valid sample has been received, then decision block 344 determines if the BrAC1 (the breath alcohol content from the initial breath test) is greater than or equal to the LLOD. If no, this test result is sent to Monitor Network 206 in block 346 and RBAM 200 is locked, and control passes to block 348 in FIG. 3D.

Referring now to FIG. 3D, in block 348 Monitor Network 206 sends a message to Supervising Agency 210 that a passed test has occurred for Offender 202 if passed tests have been selected for immediate notification (typically not the case). However, if the facial match is negative for this test, the test is labeled as Pending Review, and Monitor Network 206 sends a message to Supervising Agency 210 that a failed test with circumvention detected has occurred if this test result has been selected for immediate notification. The test results are stored in a server in Monitor Network 206. Control then returns to block 302 in FIG. 3A.

Referring back now to FIG. 3B, if decision block 344 determines that the BrAC1 is greater than or equal to the LLOD, indicating a failed breath test, then in block 350 a message is displayed to Offender 202 on OLED Display 11 asking Offender 202 to retest. Control then passes to block 352 in FIG. 3C.

Referring now to FIG. 3C, the steps enclosed within Dashed Line Box 353 encompass the Confirmation Test Routine. In block 352 the timer for the wait-to-retest period ($T_{retest}$) is started. Once $T_{retest}$ has passed, in block 354 a message is displayed to Offender 202 on OLED Display 11 asking Offender 202 to start blowing. In block 356 the timer for the confirmation testing window ($T_{ctwin}$) is started. Decision block 358 determines if $T_{ctwin}$ has expired. If yes, the test result is sent to Monitor Network 206 in block 360 and RBAM 200 is locked, and control passes to block 362 in FIG. 3D.

Referring now to FIG. 3D, in block 362 Monitor Network 206 sends a failed test message to Supervising Agency 210, which in this case was a positive initial test (indicating alcohol) that was followed by a missed confirmation test for Offender 202 if failed tests have been selected for immediate notification. However, if the facial match is negative for the initial test, the test event is labeled as Pending Review, and Monitor Network 206 sends a message to Supervising Agency 210 that a failed test with circumvention detected has occurred if this test result has been selected for immediate notification. The test results are stored in a database server in Monitor Network 206. Control then returns to block 302 in FIG. 3A.

Referring back now to FIG. 3C, if decision block 358 determines that $T_{ctwin}$ has not expired, then decision block 364 determines if a valid breath sample has been delivered by Offender 202 into RBAM 200. If no, then control returns to decision block 358 to determine if $T_{ctwin}$ has expired. If in decision block 364 a breath sample has been delivered, decision block 366 determines if the breath sample is valid. If no, then control passes to the steps within Dashed Line Box 367 encompassing the Confirmation Retry Test Subroutine. In block 370 a message is displayed to Offender 202 on OLED Display 11 asking Offender 202 to retry taking a breath test. Decision block 374 determines if $T_{ctwin}$ has expired. If no, decision block 376 determines if a breath sample has been delivered. If yes, control returns to decision block 366 to determine if the breath sample is valid. If decision block 376 determines that no breath sample has been delivered, control returns to decision block 374 which determines if $T_{ctwin}$ has expired. If yes, the result is sent to Monitor Network 206 in block 378 and RBAM 200 is locked, and control passes to block 380 in FIG. 3D.

Referring now to FIG. 3D, in block 380 Monitor Network 206 sends a failed test message to Supervising Agency 210, which in this case was a positive initial test (indicating alcohol) that was followed by an incomplete confirmation test for Offender 202 if failed tests have been selected for immediate notification. However, if the facial match is negative for the initial test, the test is labeled as Pending Review, and Monitor Network 206 sends a message to Supervising Agency 210 that a failed test with circumvention detected has occurred if this test result has been selected for immediate notification. The test results are stored in a database server in Monitor Network 206. Control then returns to block 302 in FIG. 3A.

Referring back now to FIG. 3C, if decision block 366 determines that the breath sample is valid, decision block 382 determines if the BrAC2 (the breath alcohol content from the confirmation breath test) is greater than or equal to the LLOD. If no, this result is sent to Monitor Network 206 in block 384 and RBAM 200 is locked, and control passes to block 386 in FIG. 3D.

Referring now to FIG. 3D, in block 386 Monitor Network 206 sends a passed test message to Supervising Agency 210, which in this case was a positive initial test (indicating alcohol) that was followed by a negative confirmation test for Offender 202 if passed tests have been selected for immediate notification (typically not the case). However, if the facial match is negative for the initial test or the retest, the test is labeled as Pending Review, and Monitor Network 206 sends a message to Supervising Agency 210 that a failed test with circumvention detected has occurred if this test result has been selected for immediate notification. The test results are stored in a database server in Monitor Network 206. Control then returns to block 302 in FIG. 3A.

Referring back now to FIG. 3C, if decision block 382 determines that the BrAC2 is greater than or equal to the LLOD, then decision block 388 determines if the BrAC2 is, in one embodiment, within plus or minus 0.020% of BrAC1. This value, which is a system variable not changeable by Supervising Agency 210, determines an abnormal test. When the BrAC difference between the initial test and the confirmation test is greater than 0.02%, there is most likely mouth alcohol in one or both of the tests, or it could be a different person taking one of the tests. The human body in the short period of time between the initial test and the confirmation test cannot burn off that much alcohol. The value used for abnormal tests could be any other value or predetermined criteria based on particular legal, policy, or supervisory needs. If no, then this result is sent to Monitor Network 206 in block 390 and RBAM 200 is locked, and control passes to block 392 in FIG. 3D.

Referring now to FIG. 3D, in block 392 Monitor Network 206 sends a failed test message to Supervising Agency 210, which in this case was a positive initial test (indicating alcohol) that was followed by a positive (indicating alcohol) but an abnormal confirmation test for Offender 202 if failed tests have been selected for immediate notification. However, if the facial match is negative for the initial test or the retest, the test event is labeled as Pending Review, and Monitor Network 206 sends a message to Supervising Agency 210 that a failed test with circumvention detected has occurred if this test result has been selected for immediate notification. The test results are stored in a database server in Monitor Network 206. Control then returns to block 302 in FIG. 3A.

Referring back now to FIG. 3C, if decision block 388 determines that the BrAC2 is, in one embodiment, within plus or minus 0.020% of BrAC1. This value, which is a system variable not changeable by Supervising Agency 210, could be any other value or predetermined criteria based on particular legal, policy, or supervisory needs. This result is sent to Monitor Network 206 in block 394 and RBAM 200 is locked, and control passes to block 396 in FIG. 3D.

Referring now to FIG. 3D, in block 396 Monitor Network 206 sends a failed test message to Supervising Agency 210, which in this case was a positive initial test (indicating alcohol) that was followed by a positive confirmation test for Offender 202. However, if the facial match is negative for the initial test or the retest, the test is labeled as Pending Review, and Monitor Network 206 sends a message to Supervising Agency 210 that a failed test with circumvention detected has occurred if this test result has been selected for immediate notification. The test results are stored in a database server in Monitor Network 206. Control then returns to block 302 in FIG. 3A.

The steps enclosed within Dashed Line Box 397 encompass all of the different final test results received from RBAM 200 that may be sent to Supervising Agency 210 in one embodiment, subject to modification by the results of the facial match. Other embodiments may have different final test results and use facial match results differently.

Figure 4B:
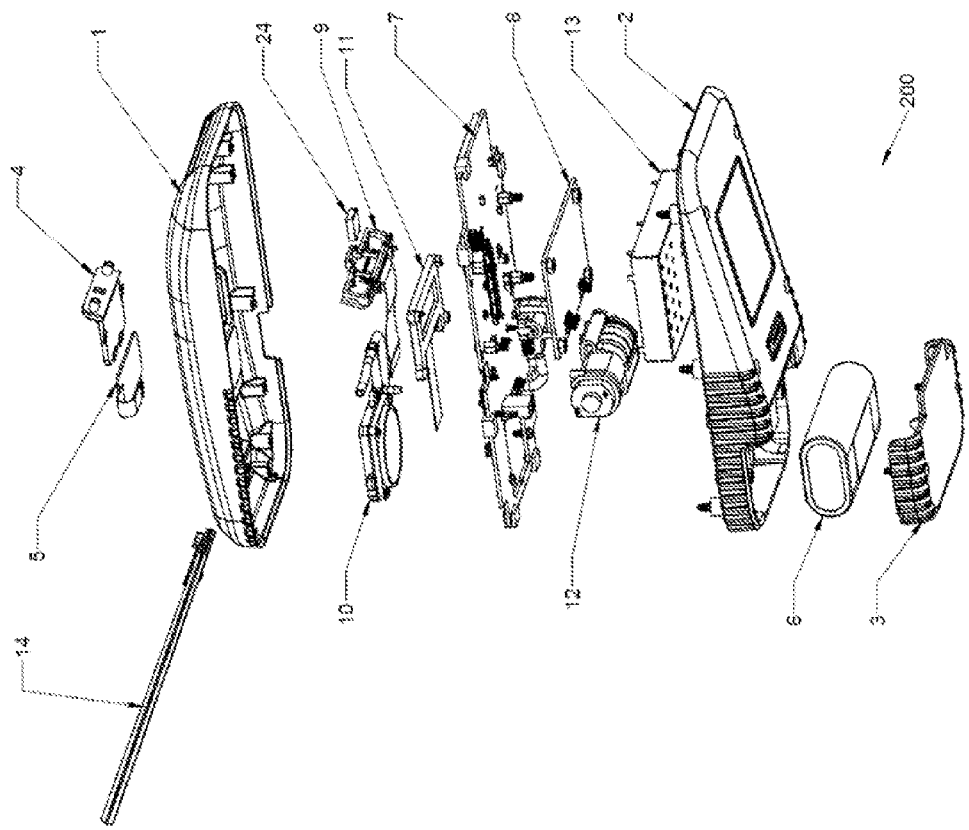
FIGS. 4A-4B show exploded views of an embodiment of a remote breath alcohol monitor.
Figure 4A:
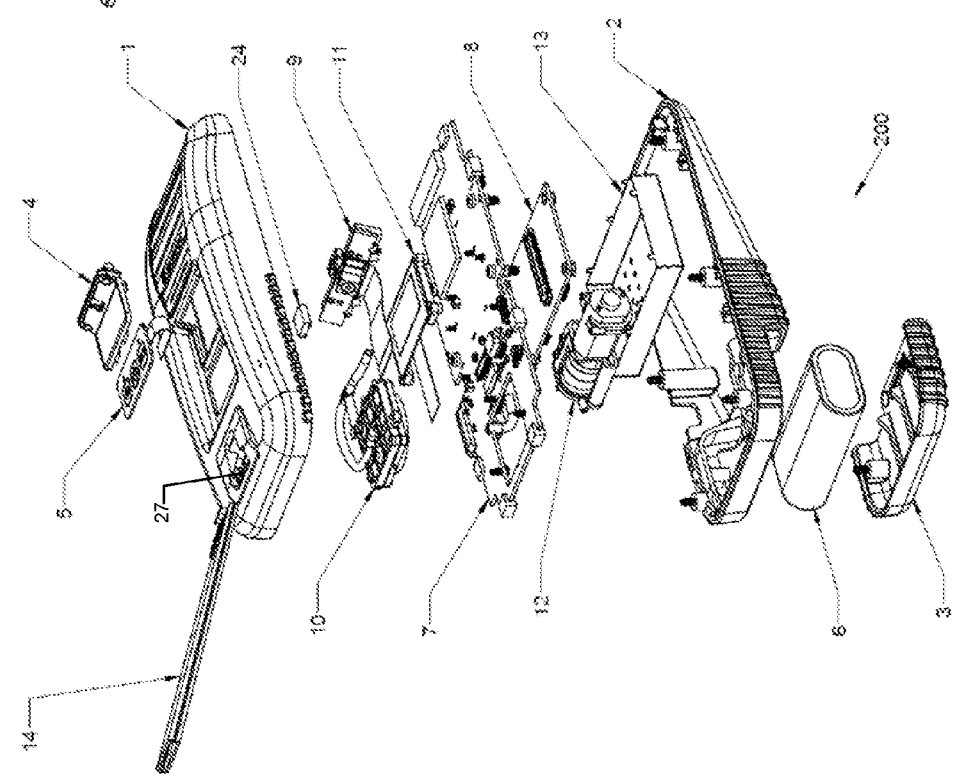

FIGS. 4A and 4B show exploded views of an embodiment of a remote breath alcohol monitor. Referring now to FIGS. 4A and 4B, RBAM 200 has a Housing Front Panel 1 and a Housing Back Panel 2. Battery Pack 6 fits within Housing Back Panel 2 and is secured within Housing Back Panel 2 by Housing Battery Door 3. Battery Pack 6 provides power for all the functions of RBAM 200. Battery Pack 6 in one embodiment is a rechargeable battery. Battery Pack 6 is not replaceable by Offender 202 but can be replaced by Supervising Agency 210 or other authorized personnel.

Window Assembly 4 and the Switch/Indicator Panel 5 fit within a midway opening in Housing Front Panel 1. Window Assembly 4 and Switch/Indicator Panel 5 are shown in more detail in FIG. 5 and are discussed in detail below.

Offender 202 is instructed to take a breath test through output displayed on OLED Display 11. In other embodiments other types of displays, sound tones, or tactile feedback, may be used to instruct Offender 202 to take a breath test. Offender 202 then inserts Breath Tube 14 into an Opening 27 in a lower portion of Housing Front Panel 1. Breath Tube 14 was designed to be flat instead of round as is typical in prior art breathalyzers on the market today. The flat design of Breath Tube 14 prevents offenders from circumventing the breath test by inserting a smaller round tube inside the larger round breathalyzer tube, and having someone else blow into the smaller round tube into the breathalyzer. There simply is no room in Breath Tube 14 to insert another tube.

When the user is instructed to blow as displayed on OLED Display 11, the breath from the user travels through Breath Tube 14 through Opening 27 and into tubing that is a part of Fuel Cell Assembly With Tubing 10. Offender 202 must blow hard enough and long enough as measured by a pressure transducer within Fuel Cell Assembly With Tubing 10 for the breath sample to be valid. Once the pressure requirement is met, Pump 12 pumps a portion of the breath sample to the fuel cell within Fuel Cell Assembly With Tubing 10. The bulk of the breath sample is vented out of RBAM 200 through Vent Opening 25 (see FIGS. 5B and 5C) in the lower portion of Housing Front Panel 1. The electrical signal registered in the fuel cell, whose signal strength is proportional to the alcohol content of the breath sample, is sent to Main Circuit Board Assembly 7. Main Circuit Board Assembly 7 in one embodiment has a low power processor from the MSP family of processors available from Texas Instruments and runs continuously, allowing Main Circuit Board Assembly 7 to perform processes in the background without waking up RBAM 200. Other embodiments could use a different processor.

The digital image taken by Camera 18 is sent to Processor Circuit Board Assembly 8. In one embodiment, Processor Circuit Board Assembly 8 has an i.MX family of processors available from Freescale Semiconductor and runs the Android operating system. Other embodiments could use a different processor, different operating system, or no operating system. Processor Circuit Board Assembly 8 runs a camera module and a wireless cellular phone module, either embedded in or connected to, Main Circuit Board Assembly 7. In one embodiment, the wireless cellular phone module is a Cinterion 3G GSM module. One skilled in the art will recognize that a CDMA module could also be used, as well as other wireless communication technologies including Wi-Fi, Bluetooth, ZigBee, and others. In one embodiment, the Processor Circuit Board Assembly processes the image from the camera to perform facial matching. Thus the software for performing facial matching is run on Processor Circuit Board Assembly 8 in RBAM 200 as opposed to sending the image over a communications network to a central server for facial match processing. In another embodiment, the facial matching software is stored on a server at Monitoring Network 206 and the image may be uploaded to Monitoring Station 208 to perform facial matching. In another embodiment, part of the facial matching process is performed on Processor Circuit Board Assembly 8 in RBAM 200 and part by Monitoring Network 206. In another embodiment, facial matching may be performed by a third party service provider. That is, data required for facial matching is communicated to the third party service provider, and the results of the facial match are communicated by the third party service provider back to RBAM 200 or Monitoring Network 206 or both. The image uploaded may be at a lower resolution than what the facial matching software uses to perform a facial match. The lower resolution image saves on uploading costs but still gives Supervising Agency 210 personnel the ability to compare the uploaded image with an enrollment image to verify that the right person took the breath test.

Liveness face detection can prevent breaching the system with printed photographs of Offender 202 placed in front of RBAM 200. Liveness face detection takes a video, or several different still images, to detect eye movement, mouth movement, etc., to determine that a real face is being viewed prior to taking the image when Offender 202 is blowing into Breath Tube 14. Due to its high power consumption, Processor Circuit Board Assembly 8 is only powered on when needed, such as when a breath sample is being taken, an image is taken and processed for facial recognition, and the results are sent via the wireless cellular phone module to Monitor Network 206. Through GPS technology in the wireless cellular phone module, or through backup location technologies available from the cellular carrier's network, the location fix of Offender 202 is also transmitted to Monitor Network 206. Power management in RBAM 200 is unique, using a low power processor to perform some functions coupled with a high power processor to perform other functions, in order to conserve battery power. Other embodiments could use just a single processor instead of the two processors described herein. Processor Circuit Board Assembly 8 is protected from radio frequency electromagnetic radiation by RF Shield 13.

Figure 5C:
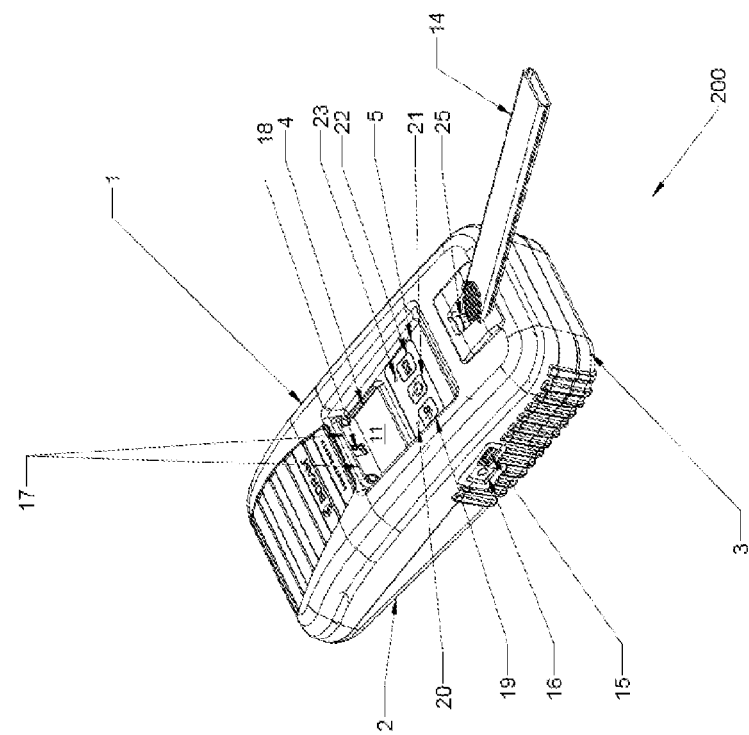
FIGS. 5A-5C show various assembled views of an embodiment of a remote breath alcohol monitor.
Figure 5B:
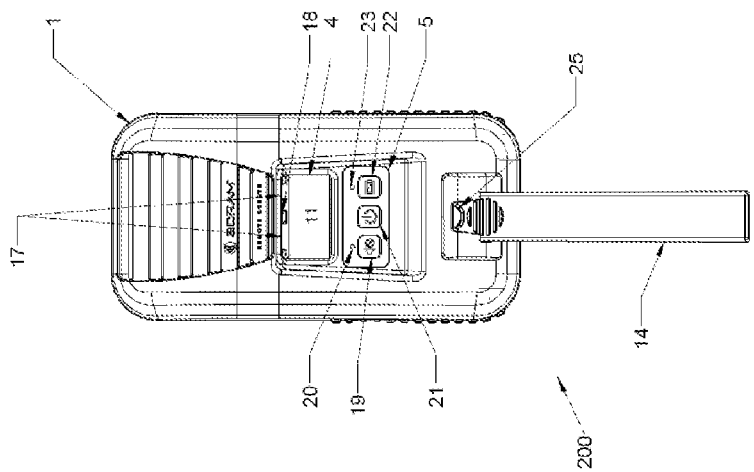
Figure 5A:
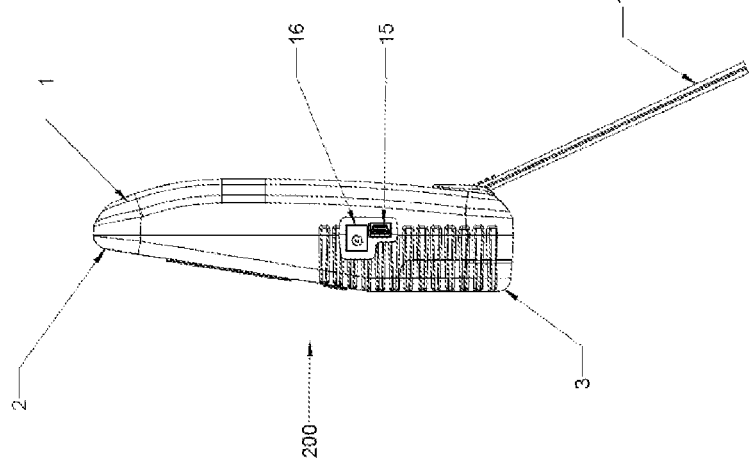

FIGS. 5A-5C show various assembled views of an embodiment of a remote breath alcohol monitor. Referring now to FIGS. 5A-5C, USB and Ethernet Connector 15 allows RBAM 200 to be connected to a PC so that a variety of functions can be performed, such as firmware upgrades, diagnostic testing, troubleshooting, calibration, etc. The PC accesses Monitor Network 206 via Internet 216 to download firmware updates and onto RBAM 200 through USB and Ethernet Connector 15. Charging Connection 16 allows RBAM 200 to be plugged in to a charger (not shown) to recharge Battery Pack 6.

Mirrors 17 in Window Assembly 4 help Offender 202 to properly align Offender 202's face so that an image can be taken with Camera 18 mounted within Camera Circuit Board Assembly 9. If Offender 202 can see his/her face in the Mirrors 17, then Offender 202 knows that he/she has achieved correct alignment with RBAM 200. The lens of Camera 18 seats within an opening in Window Assembly 4 between Mirrors 17. In one embodiment, Camera 18 is a high resolution camera, capable of taking both still images and video, using CMOS technology. Other embodiments can use other types of cameras such as CCD devices. While Offender 202 is delivering a breath sample, Camera 18 in Camera Circuit Board Assembly 9 takes an image of Offender 202. One skilled in the art will recognize that it may not be practical to take the image at the precise instant the breath sample is delivered, so this image could be taken at the beginning, middle, end, or any reasonable time period before or after the instant the breath sample is delivered. The Camera Circuit Board Assembly may have light sensors in it to adjust the camera module to the current lighting environment, or it may always use a flash regardless of the current lighting environment to control the exposure. The length of Breath Tube 14 is designed to place the face of Offender 202 at the right focal distance from the lens of Camera 18, which is approximately eight inches. In addition, the flat design of Breath Tube 14 prevents Offender 202 from tilting her/her head too much from side-to-side. Movement from side-to-side needs to be limited to no more than about ten degrees for facial recognition purposes. OLED Display 11 of Switch/Indicator Panel 5 will output, at various times, various commands, status, and information to Offender 202.

Figure 10:
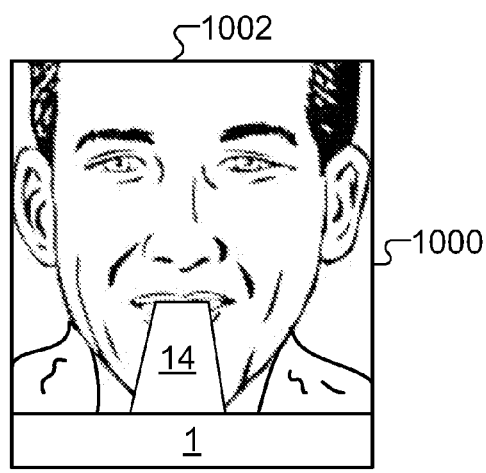
FIG. 10 shows an example of a digital image of a user giving a breath sample taken by the camera in a remote breath alcohol monitor in an embodiment of remote breath alcohol monitoring.

FIG. 10 shows an example of a digital image of a user giving a breath sample taken by the camera in a remote breath alcohol monitor in an embodiment of remote breath alcohol monitoring. Referring now to FIG. 10, a user is holding RBAM 200 and has inserted the open end of breath tube 14 into the user's mouth and begins to blow. Camera 18 takes a digital image 1000 of the user, which shows at least a portion of the user's face 1002, a portion of the breath tube 14, and a portion of the housing front panel 1 that are within the field of view of camera 18. Substantially all of the user's face is captured, except for the top of the head and the portion of the chin blocked by breath tube 14.

Switch/Indicator Panel 5 has Mute Switch 19 that Offender 202 can press to mute Speaker 24 at any time. Visual Speaker Indicator 20 turns red when muted. Pressing Mute Switch 19 again will un-mute Speaker 24.

Switch/Indicator Panel 5 also has Power On/Off Switch 21. Offender 202 can press and hold Power On/Off Switch 21 for a few seconds to force RBAM 200 to power on and check in with Monitor Network 206, and then RBAM 200 will turn itself off after downloading any schedule changes or other information.

Switch/Indicator Panel 5 also has Battery Indicator 22. Visual Battery Indicator 23 turns red when Battery Pack 6 needs charging. When plugged in and charging, Visual Battery Indicator 23 turns yellow, and turns green when fully charged and still plugged in via Charging Connection 16 to the charger. When fully charged and unplugged, no color is displayed by Visual Battery Indicator 23. RBAM 200 will notify Monitor Network 206 if the remaining life of Battery Pack 6 is estimated to be less than a certain percent of battery capacity. RBAM 200 may also provide tactile feedback (vibration) to Offender 202 at various points of operation.

Figure 8:
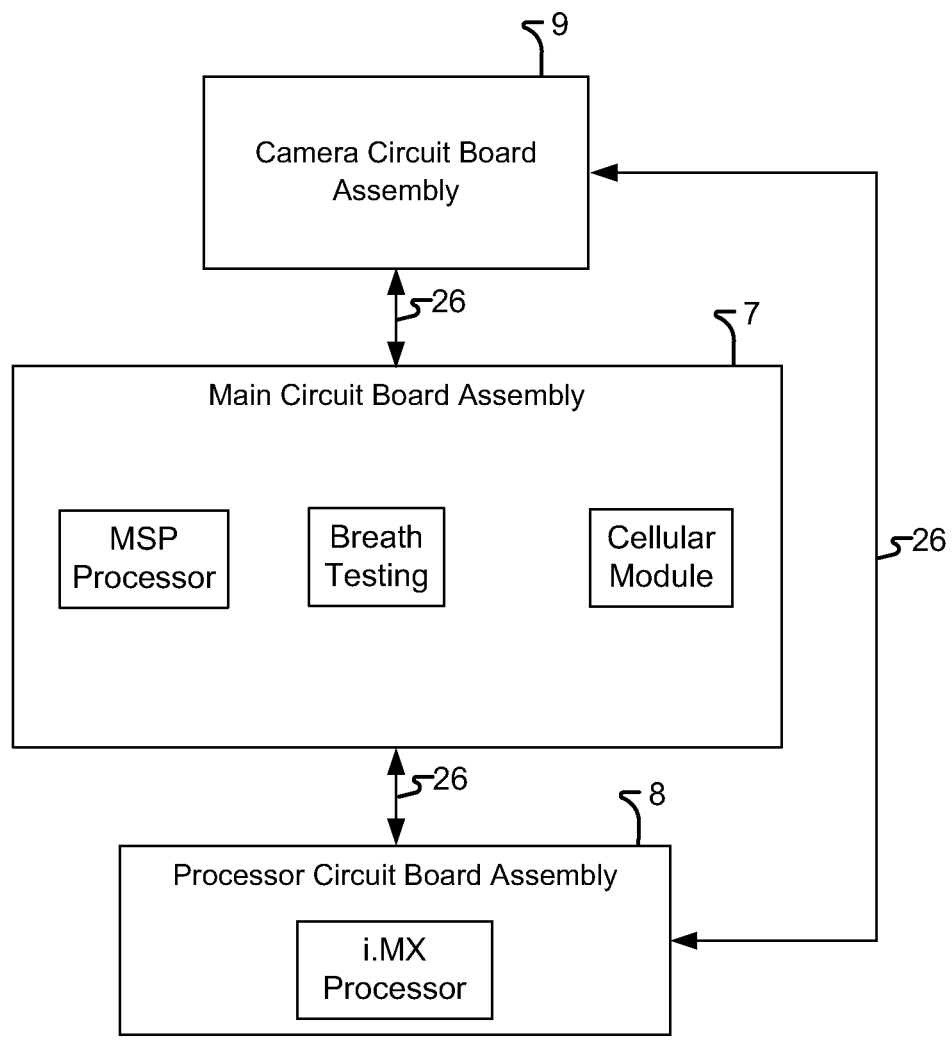
FIG. 8 shows a block diagram of the circuit boards in an embodiment of a remote breath alcohol monitor.

FIG. 8 shows a block diagram of the circuit boards in an embodiment of a remote breath alcohol monitor. Referring now to FIG. 8, Main Circuit Board Assembly 7, Processor Circuit Board Assembly 8, and Camera Circuit Board Assembly 9 communicate with each other through Connectors 26. These could all be on one circuit assembly, two circuit assemblies, or any other number as a design choice. The MSP low power processor, the breath testing components, and the cellular phone module are all physically located on Main Circuit Board Assembly 7. The MSP processor controls the scheduling of breath tests and initiates communication with Monitor Network 206 through the cellular phone module. The i.MX processor is physically located on Processor Circuit Board Assembly 8. The i.MX processor controls the taking of a breath sample, taking the image, and in one embodiment, performing facial matching, and certain communications with Monitor Network 206.

Figure 6:
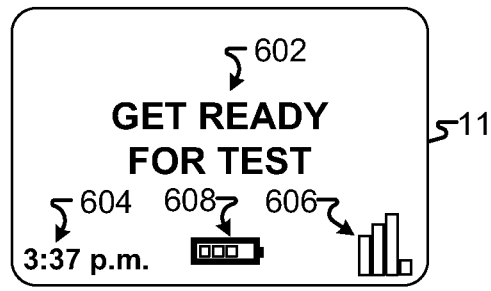
FIG. 6 shows a screen capture from the display in an embodiment of a remote breath alcohol monitor.

FIG. 6 shows a screen capture from the display in an embodiment of a remote breath alcohol monitor. Referring now to FIG. 6, when on, OLED Display 11 will display various messages to Offender 202 during a course of operation, such as Message 602. The Time of Day 604 from the clock within RBAM 200 may also be displayed along with the Cellular Signal Strength 606 which is displayed with one to four vertical bars when OLED Display 11 is on. Battery Strength 608 is displayed with one to four boxes when OLED Display 11 is on.

Described now is just one series of messages. One skilled in the art will recognize that many different messages for many different purposes may be programmed into the operation of RBAM 200, and this discussion is simply exemplary of one purpose, and the individual messages may be different from that described below.

For a typical breath test, a series of sequential Messages 602 are displayed on OLED Display 11 which are encompassed in the steps shown in blocks 316, 332, 350, 354, and 370 in FIGS. 3B and 3C. The first Message 602, "PLEASE WAIT" is displayed for a short period of time before the test. When it is time to begin the test, Message 602 will change to "BLOW" and is displayed on OLED Display 11 (block 316 in FIG. 3B). If after a certain period of time, such as two minutes, if Offender 202 has not begun to blow, a sound, such as a beep, and/or a tactile output, such as a vibration are output from RBAM 200. The sound and/or vibration are repeated periodically, such as every two minutes, until $T_{grace}$ expires or Offender 202 begins to blow. A short time after Offender 202 begins to blow, Message 602 changes to "STOP" and is displayed on OLED Display 11. When RBAM 200 determines that a valid sample has been received, Message 602 then changes to "ANALYZING DATA." Message 602 then changes to "TEST COMPLETE." Message 602 then changes to "SHUTTING DOWN" and OLED Display 11 goes dark when shut down is complete.

If RBAM 200 determines that an invalid sample has been received, Message 602 changes to "BLOW STEADY" and is displayed on OLED Display 11 (block 332 in FIG. 3B). In addition, a sound and/or vibration may be output to Offender 202.

If the BrAC measured is greater than the LLOD, the $T_{retest}$ period of time must pass before a retest can be performed. If there is a negative facial match upon taking the breath test, a second test can be taken right away without having to wait for the $T_{retest}$ period of time to pass. Typically, RBAM 200 will not output any reasons to Offender 202 as to the nature of the failure that requires a retest (i.e., negative facial match, BrAC limit exceeded, etc.). If a retest is required, Message 602 is changed to "RETEST IN 3 MIN" (where $T_{retest}$ is three minutes) and is displayed on OLED Display 11 (block 350 in FIG. 3B). One minute later, Message 602 is changed to "RETEST IN 2 MIN." One minute later, Message 602 is changed to "RETEST IN 1 MIN." When it is time to begin the test, Message 602 will change to "BLOW" (block 354 in FIG. 3C) and is displayed on OLED Display 11 and the sequence above is repeated.

If a valid sample is not received, then Message 602 will change to "BLOW STEADY" (block 370 in FIG. 3C) and is displayed on OLED Display 11 and the sequence above is repeated. In addition, a sound and/or vibration may be output to Offender 202. RBAM 200 will upload the test results to Monitor Network 206, and then turn itself off.

FIGS. 7A-7D show a flow chart of a general method of implementation in an embodiment of remote breath alcohol monitoring. Referring now to FIGS. 7A-7D, the set up process begins in block 702, typically at Supervising Agency 210. Supervising Agency 210 may be a court, government agency, law enforcement agency, or private corrections service provider working in conjunction with a local judicial district to handle a variety of offenders associated with DUI/DWI, probation, specialty courts, family courts, and underage drinking. In block 702 Supervising Agency 210 adds a new client, such as Offender 202, through the website available over the Internet 216 at Monitor Network 206. Based upon the circumstances and/or court orders associated with Offender 202, a schedule for taking breath tests is established, which may be a fixed schedule, a random schedule, a flexible schedule, or any combination of the above. A fixed schedule would require a test at a fixed time, such as 8:00 am on a particular day. For a random test schedule, personnel at Supervising Agency 210 through the user interface for the website for setting up a new client select a window of time during the day, such as three hours as a default time, and a random time during that three hour block will be generated for taking a breath test. For a flexible schedule, a window of time is selected (e.g., 10:00 am to 1:00 pm), and Offender 202 can provide a breath test any time within that window. The schedule may also be provisioned to receive on-demand breath tests. The cell phone number of Offender 202 is also associated with the schedule. When a scheduled test is eminent, a text message or cell phone call can be made to the cell phone number of Offender 202 as a courtesy reminder to Offender 202 that there is an upcoming breath test. In another embodiment, Offender 202 may turn RBAM 200 on whenever they want and take a breath test, either instead of a test schedule, or in addition to a test schedule.

In block 704 an RBAM 200 is assigned to Offender 202. The serial number of the RBAM 200 is associated with the name of Offender 202. The wireless capability of the RBAM 200 is activated on the wireless network through a wireless carrier or intermediate wireless service provider, and RBAM 200 is powered on. In block 706 the assigned RBAM 200 communicates with Monitor Network 206 and the schedule and other settings that were established for Offender 202 are downloaded from Monitor Network 206 to RBAM 200 and stored. A supervisory person or agent associated with Supervising Agency 210 could also perform the set up process from a laptop in the field as long as a connection to Internet 216 is available. Alternatively, RBAM 200 can simply be mailed to Offender 202 who powers it on and as long as a connection to Cellular Network 204 is available, the schedule and other settings for Offender 202 may be downloaded from Monitor Network 206 to RBAM 200.

The enrollment process begins in block 708 where Offender 202 will take a breath test. Offender 202 may first be required or offered the opportunity to review some training materials (printed matter, videos, etc.) on how to use RBAM 200. Offender 202 blows through Breath Tube 14, RBAM 200 takes an enrollment image of Offender 202. An enrollment template is extracted from the enrollment image and that enrollment template will be used as a comparison for future tests. The template is a mathematical model that reflects the characteristics of the facial image. There are critical factors/numbers when performing a facial match, such as the distance between the pupils (typically the most critical feature), the shape of the face and facial features, the location of the nose and mouth with respect to each other and the pupils, the shape of the eyes, etc. The template defines these critical factors/numbers. Every image taken during a breath test has a template extracted from the image, and that template is compared to the enrollment template for facial matching. The location fix where the test was taken is also captured for the breath test. The facial matching software processes the image taken in block 710 and generates a quality score for the image. Decision block 712 determines if the quality score is greater than or equal to a predetermined image quality score deemed to be of high enough quality to serve to extract a template for future facial matching purposes. If not, output is sent to OLED Display 11 or to Monitor Network 206 requesting to take another test so that another image can be taken. Once the facial matching software determines that a sufficiently high quality image has been taken, it extracts a template that is stored on RBAM 200 to be used for facial matching of future tests provided by Offender 202. Next, in block 714 (see FIG. 7B) the enrollment image is uploaded to Monitor Network 206 which stores the enrollment image associated with Offender 202. This enrollment image is also typically used for human comparison if needed, and a lower resolution version of this image is often all that is required to do so. Other embodiments may upload enrollment images to the Monitor Network 206 and have Monitor Network 206 generate quality scores, do the template extraction, and store the enrollment template. Additional embodiments may perform some of these functions on RBAM 200 and others on Monitor Network 206, or even perform them in both places.

The training process in block 716 enables Offender 202 to practice holding RBAM 200 properly, lining up RBAM 200 properly with the eyes or nose as reflected in Mirrors 17, and practice blowing so Offender 202 can learn to not blow too hard but also not blow too softly. When Offender 202 is finished with training, by holding down the Power On/Off Switch 21 for five seconds, or after five minutes of inactivity, the training mode will stop.

The normal operation process begins in block 718 where RBAM 200, in one embodiment, checks in every twenty minutes with Monitor Network 206 to see if any changes to the settings, the schedule, or if an on-demand test has been ordered. The check-in interval is chosen based on trade-offs between immediacy of pulling new data down to RBAM 200 and power consumption, and any interval could be used. Changes are uploaded to RBAM 200 in block 720. When it is time for a scheduled test in block 722, a prompt may be sent in block 724 to Offender 202 via a text message or a phone call with a pre-recorded message to the cell phone associated with Offender 202. In block 726, when the scheduled time arrives, RBAM 200 turns on and sends a prompt to Offender 202 to begin blowing into Breath Tube 14 of RBAM 200 as described above in more detail in reference to FIG. 6. In block 728 (see FIG. 7C) Offender 202 blows into Breath Tube 14 inserted into RBAM 200, a still image is taken by Camera 18, the breath sample is processed by Fuel Cell Assembly With Tubing 10, and the location fix is obtained. The facial recognition software analyzes the facial image and determines a quality score for the image and creates a template for this test. If the quality score of the image does not meet a threshold value, no facial recognition attempt will be made. The template for this test is compared to the template extracted from the enrollment image taken in block 708 and stored in memory in Processor Circuit Board Assembly 8, and a match score is determined. The match score must meet certain predefined criteria to be considered a facial match. In one embodiment the match score must be above a predefined threshold value to be considered a facial match. Raising the acceptable threshold value would force a stricter match, and lowering the threshold value would loosen the criteria to declare a match. The goal is to set the predetermined criteria to minimize false rejections when Offender 202 did indeed take the test, and also minimize false acceptance of a match when Offender 202 did not take the test. In one embodiment of the invention, the image taken by Camera 18 is uploaded to Monitor Network 206 and facial matching is done at Monitor Network 206, or, just the template is uploaded to be compared with the enrollment template stored at Monitor Network 206, or any combination. In another embodiment, when Offender 202 begins blowing, prior to taking the image required for facial matching, Camera 18 first begins taking a video or series of still images of Offender 202 to be analyzed by a liveness detection component of the facial recognition software, which analyzes the video or series of images to determine movement of the eyes, eyebrows, nose, mouth, etc. A printed photograph or mask placed in front of RBAM 200 will not have any movement of these facial parts.

In decision block 730, based upon the results of the breath test, facial match result, or quality score of the image taken, RBAM 200 may output a message through OLED Display 11 to Offender 202 to retake the breath test in block 732. A retest is typically required for a positive breath test and may be required for a poor quality score or negative facial match. For a poor quality score or a negative facial match a series of messages 602 are displayed to Offender 202 on OLED Display 11 (like that shown in FIG. 6) such as: "AVOID DIRECT SUNLIGHT," "CLEAR FACE OF OBSTRUCTIONS," "STAND OR SIT UP STRAIGHT," and "BREATH TUBE MUST BE LEVEL," or any other message deemed useful in helping Offender 202 take a better image. Each message is displayed for about three seconds. These messages remind Offender 202 how to correctly give a breath test and capture a high quality digital image of Offender 202.

The retest is evaluated again in decision block 730. If there is a facial match, and the quality score of the image is acceptable, and a negative breath test, RBAM 200 in block 734 will send to Monitor Network 206 the results of both tests (BrAC; location fix; and images, match score, templates, and the quality scores from the facial recognition analysis). (See FIGS. 3A-3D for details on the different test results that may be sent to Monitor Network 206.)

The analyze operation begins in block 736 where Monitor Network 206 will analyze the test results received: a single test; or, a test and a retest that are combined into a single test event. The outcome of the initial test may be one of the following: missed, incomplete, passed, or failed along with a positive facial match or a negative facial match, and the location fix. For a missed test, Offender 202 never attempted to blow into RBAM 200. An incomplete test is the result of Offender 202 attempting to blow but failing to deliver a valid sample. This may be the result of Offender 202 not blowing hard enough, or not blowing long enough, or some other reason that results in the failed delivery of a valid sample. For a valid sample, the result is either passed or failed based upon the BrAC level. A positive facial match indicates that the person delivering the sample is the Offender 202 enrolled with the RBAM 200. A negative facial match may be the result of a different person delivering the valid sample. Or, even if Offender 202 delivered the valid sample, a negative facial match may result due to Offender 202 wearing sunglasses, hair covering the face, or other obstruction such as a hat or scarf.

Monitor Network 206 will report a single missed test result as "Missed"; a single incomplete test result as "Incomplete"; a single passed test with a positive facial match as "Passed"; and a single passed test with a negative facial match as "Needs Review". Needs Review test results may be set to be an immediate notification to Supervising Agency 210.

A failed test is automatically followed by a confirmation test. The possible outcomes for a confirmation test are the same as for an initial test. The confirmation test is the opportunity afforded to Offender 202 to prove that the failed first test was mouth alcohol (such as mouthwash) and not a result of the consumption of alcohol. In the embodiment in which facial matching is performed on RBAM 200, a retest may also be required for a negative facial match.

For a combined test (failed initial test followed by a confirmation test), Monitor Network 206 will report a missed confirmation test as "Failed" (a positive initial test followed by a missed confirmation test (see Block 362 in FIG. 3D)). Offender 202 had the opportunity to take the confirmation test, but did not. Monitor Network 206 will report a missed confirmation test as "Failed". Monitor Network 206 will report an incomplete confirmation test as "Failed" (a positive initial test followed by an incomplete confirmation test (see Block 380 in FIG. 3D)). Offender 202 had the opportunity to take the confirmation test, but failed to deliver a valid sample. Monitor Network 206 will report a negative confirmation test as "Passed" (a positive initial test followed by a negative confirmation test (see Block 386 in FIG. 3D)). Monitor Network 206 will report a positive but abnormal confirmation test as "Failed" (a positive initial test followed by a positive but abnormal confirmation test (see Block 392 in FIG. 3D)). Monitor Network 206 will report a positive confirmation test as "Failed" (a positive initial test followed by a positive confirmation test (see Block 396 in FIG. 3D)). In this scenario, the delta between the two tests is less than or equal to 0.02%.

Location fix is determined with each test. In one embodiment this is accomplished by obtaining the GPS coordinates, which are obtained using a GPS receiver. The GPS receiver may be a stand-alone component within the RBAM, or may be built into the cellular module. However, in some cases, typically if Offender 202 is indoors, the satellite signal needed to get the GPS coordinates cannot be obtained and several secondary methods may be used. In one embodiment those secondary methods include cell tower triangulation by RBAM 200 and the cellular service provider. If this option is not available, then in one embodiment, location fix is determined by the nearest cell site.

Different types of test results can be sent on an immediate or priority notification basis using Communication Link 222 if Supervising Agency 210 elects to be so notified. For example, Supervising Agency 210 can elect to be notified immediately for failed tests, missed tests, incomplete tests, and needs review. Even if immediate notification is not chosen, all test results are uploaded to Monitor Network 206 upon completion of the test and stored and are immediately available for review by Supervising Agency 210 via the website. An agent at Supervising Agency 210 may review the uploaded data in different ways. For all Offenders 202 being monitored, all their test results can be displayed in the order the tests were uploaded, with the oldest test results on the top of the list, or, with the newest test results on the top of the list. The list can also be sorted by individual Offender 202, oldest tests on top or newest tests on top.

For an agency level view, only alerts and exceptions may be displayed. This exception based monitoring makes more efficient use of agent's time by focusing agent attention on the tests that matter. All failed, missed, incomplete, and needs review test results can be displayed for the agent, and as the agent deals with each one, the action taken can be logged and the alert or exception resolved. Alerts can include no communication by RBAM 200 with Monitor Network 206 for a given period of time, tamper alerts, and housing breach alerts. Without facial matching, prior art systems had to report everything to a supervising agency and every single one of the tests needed to be looked at and evaluated. Facial matching coupled with automatic confirmation testing eliminates a lot of data that no longer needs to be reviewed by an agent at Supervising Agency 210. This exception based reporting as disclosed herein is a tremendous improvement over existing remote breath monitoring systems. In addition, when Offender 202 is confronted with a failed test, the date and time, the BrAC, their facial image, and their location fix, it makes it very difficult for Offender 202 to deny what they did.

Immediate notification may be accomplished in the following ways: by text message; by email; or by a page sent to a pager. Supervising Agency 210 can then take whatever action they desire. An agent for Supervising Agency 210 may call Offender 202 and inquire as to why Offender 202 missed taking the test. For a missed test, Supervising Agency 210 may have information that Monitor Network 206 does not. For example, Offender 202 may have called in and said they could not take the test for whatever reason.

Upon notification of a missed test, or for some other reason, Supervising Agency 210 may request an on-demand test. An agent for Supervising Agency 210 can click a button on their web application ordering an on-demand test for Offender 202. Since RBAM 200 checks in with Monitor Network 206 periodically, RBAM 200 will receive the on-demand test order within its check-in interval, wake up, and prompt Offender 202 to take a test. Monitor Network 206 may also send a text message to Offender 202, or the agent may call Offender 202 immediately after the on demand test is ordered in the web application. The text message or agent will then instruct Offender 202 to hold down Power On/Off Switch 21 for five seconds, which causes RBAM 200 to power up and communicate with Monitor Network 206, receive the on-demand test order, and prompt Offender 202 to take a test.

In block 738 the test results are stored and are immediately available for review by an agent at Supervising Agency 210. Decision block 740 determines if an immediate or priority notification is necessary based upon preferences established by Supervising Agency 210. If yes, then in block 742 notification is sent from Monitor Network 206 to Supervising Agency 210 or to a specific agent or supervisor associated with Supervising Agency 210 via communication link 222. Control returns to block 736 to await the next test results needing analysis. If immediate notification is not needed, then in block 744 (see FIG. 7D) if there are any changes to the settings or schedule, those changes are downloaded to RBAM 200. RBAM 200 will then turn off and control returns to blocks 718 (check in every fifteen to twenty minutes), 722 (wait for next scheduled test), and 724 (send reminder text message) (see FIG. 7B).

When Offender 202 no longer needs to be monitored as determined by Supervising Agency 210, in block 745 RBAM 200 is unassigned from Offender 202. In block 746 monitoring is stopped and Offender 202 returns RBAM 200 to Supervising Agency 210. In block 748 Monitor Network 206 will communicate with RBAM 200 and in block 750 check RBAM 200 back into inventory, where it becomes available to the next Offender 202, and RBAM 200 is deactivated from the wireless network. After RBAM 200 is deactivated from the wireless network the method ends.

Figure 9:
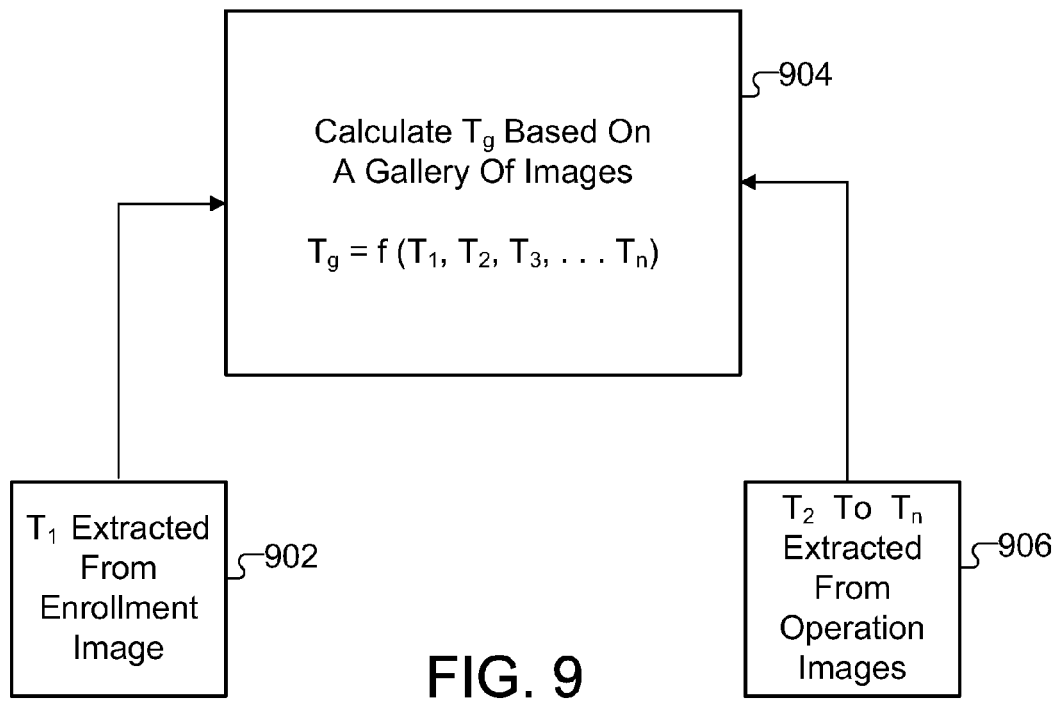
FIG. 9 shows a block diagram of using a gallery of images for facial matching in another embodiment of remote breath alcohol monitoring.

FIG. 9 shows a block diagram of using a gallery of images for facial matching in another embodiment of remote breath alcohol monitoring. Referring now to FIG. 9, in another embodiment of the RBAM, facial matching is accomplished by comparing the template from the test image to a template derived from a gallery of images, as opposed to just comparing it to a template extracted from a single enrollment image. Block 902 represents the enrollment process defined by steps 708-714 in FIGS. 7A and 7B, and block 906 represents the operation process defined by steps 718-734 in FIGS. 7B and 7C.

Figure 7A:
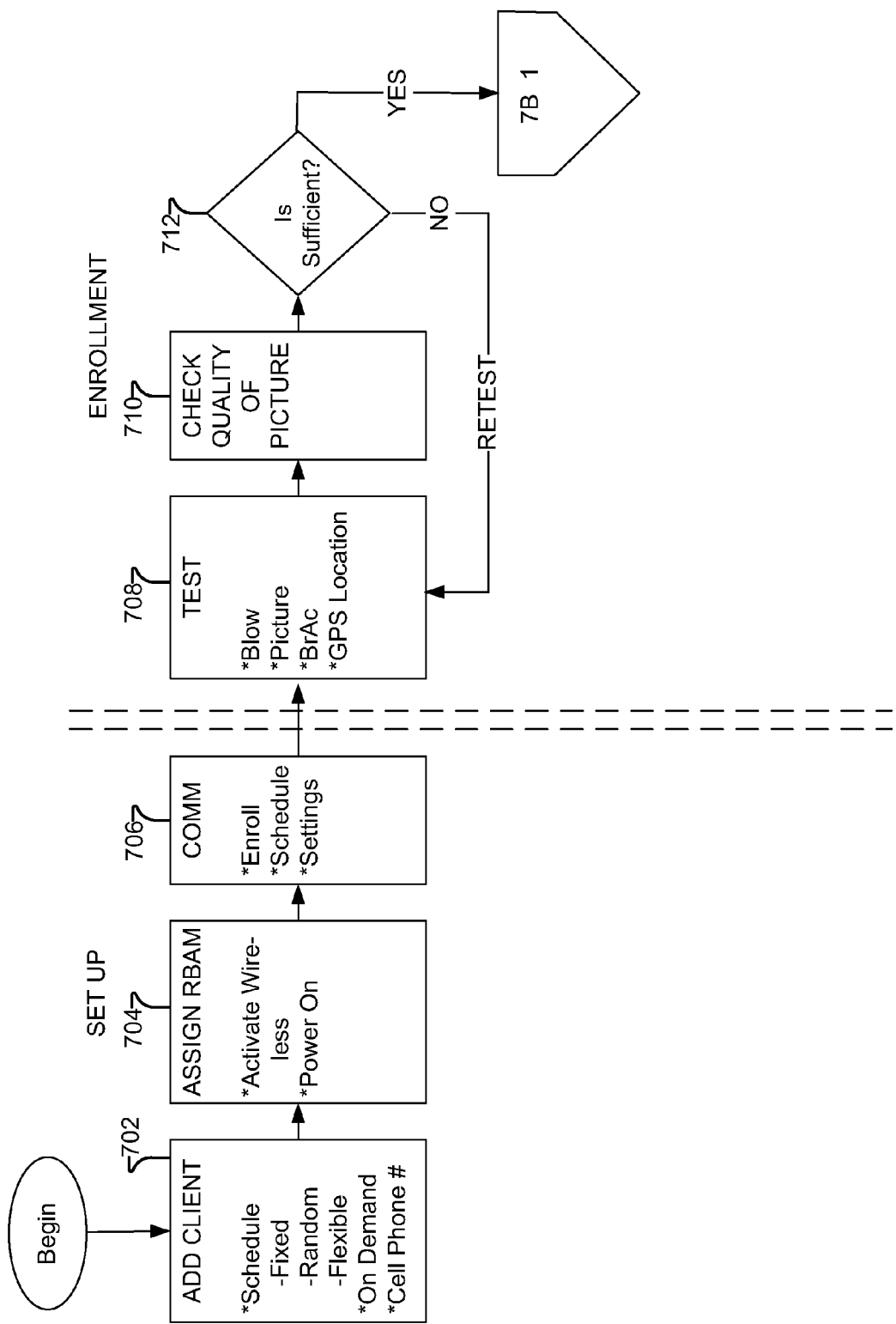
FIGS. 7A-7D show a flow chart of a general method of implementation in an embodiment of remote breath alcohol monitoring.
Figure 7B:
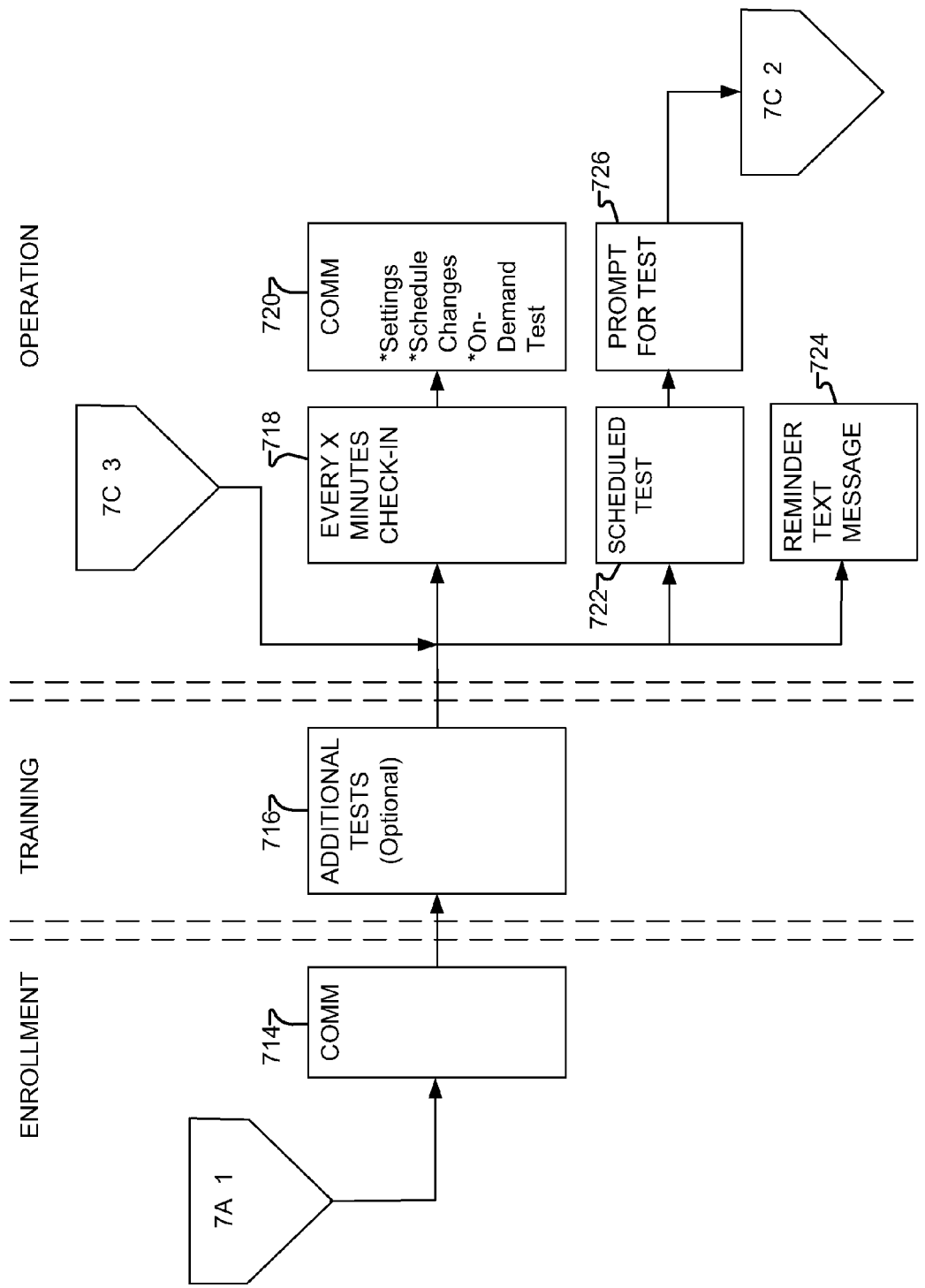
Figure 7C:
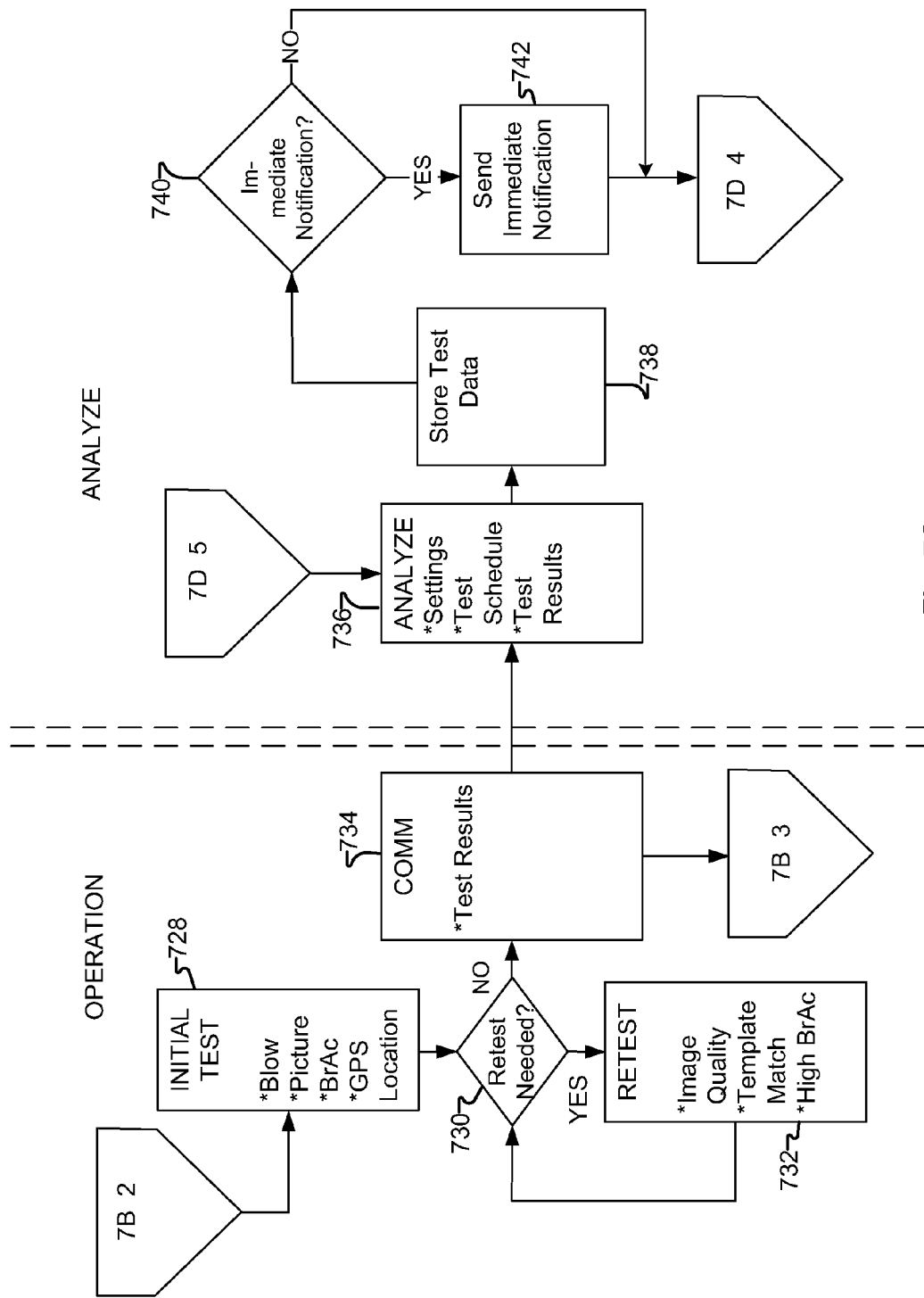
Figure 7D:
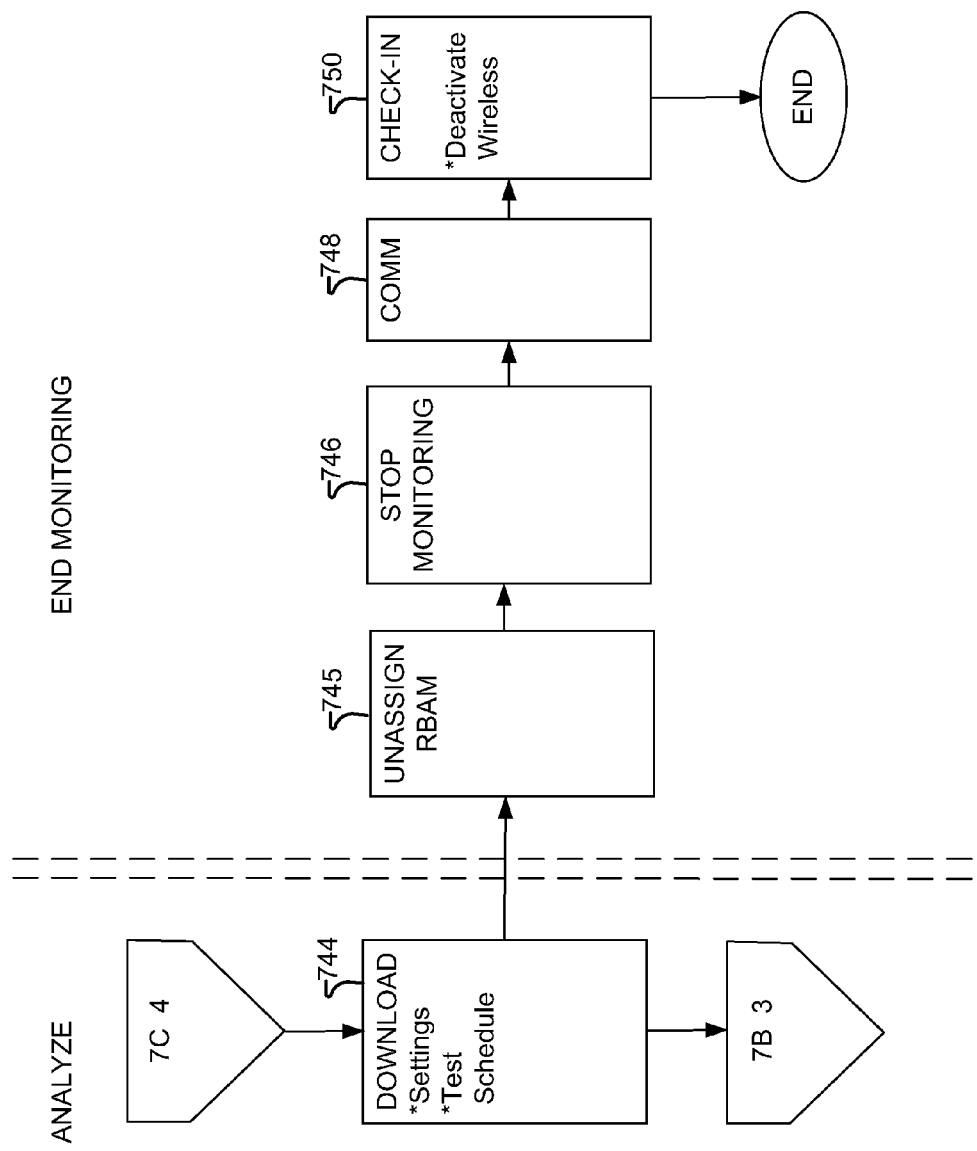

During enrollment in block 902, a template is still extracted from the image taken in block 708 if the quality of the image (block 710) is determined to be sufficient (block 712) (see FIG. 7A). This template is referred to as $T_1$, and it is the first of multiple templates that will be used to calculate a gallery matching template $T_g$ in block 904. Until additional templates are added to the gallery in block 904, $T_g$ is the same as $T_1$.

During normal operation in block 906 (see FIG. 7C), for a first test, a template is extracted from the image taken in blocks 728 and/or 732 if the quality of the image is determined to be sufficient. This template is compared to the current calculated $T_g$, which at this time is the same as $T_1$. This template, designated as $T_2$, may be added to the gallery in block 904. $T_g$ is then recalculated as a function of both $T_1$ and $T_2$.

For the next test during normal operation, a template, $T_3$, is extracted from the image taken in blocks 728 and/or 732 if the quality of the image is determined to be sufficient. For this test, to determine if there is a facial match, instead of just comparing $T_3$ to a template extracted from a single enrollment image, $T_3$ is compared to the current calculated $T_g$, which at this time is $f(T_1, T_2)$ as shown in block 904.

This process continues with $T_g$ being recalculated each time an additional template from subsequent tests are added to the gallery in block 904. $T_g$ is therefore a function of $T_1$, $T_2, T_3 \ldots T_n$, where n is the maximum number of templates desired in the gallery. In one embodiment, n=20 templates as testing demonstrated that the incremental value in storing more images and their templates did not significantly improve or enhance functionality. But in practice n could be any number.

The decision to include each subsequent template $T_n$ in the gallery can be based on several criteria including the image quality score, or whether the template successfully matched with $T_g$. The criteria need not be the same for each new template that is added to the gallery. For example the criteria used to determine if $T_{20}$ is included may be different than the criteria used to determine if $T_2$ is included in the gallery. The criteria may be scaled to become more demanding with each additional template added. Templates $T_1$ to $T_n$ may be calculated and stored on a server in Monitor Network 206, or on RBAM 200, or a combination thereof.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. It will be understood by those skilled in the art that many changes in construction and circuitry and widely differing embodiments and applications will suggest themselves without departing from the scope of the disclosed subject matter.

What is claimed is:

1. A method for remote breath alcohol monitoring comprising the steps of:
    (a) analyzing by a remote breath alcohol monitor a first breath sample for a first breath alcohol content;
    (b) capturing a first digital image of at least a portion of a face of a person providing the first breath sample;
    (c) performing a first facial match on a first template extracted from the first digital image of the person compared to a gallery template derived from a gallery of images of the person; and
    (d) sending by the remote breath alcohol monitor at least one of the first breath alcohol content and a result of the first facial match to a monitor network.

2. The method for remote breath alcohol monitoring according to claim 1 further comprising the step of:
    receiving the first breath sample in the remote breath alcohol monitor.

3. The method for remote breath alcohol monitoring according to claim 1 wherein capturing step (b) further comprise the step of:
    capturing the first digital image with a camera in the remote breath alcohol monitor.

4. The method for remote breath alcohol monitoring according to claim 1 wherein performing step (c) further comprise the step of:
    performing the first facial match by at least one of the remote breath alcohol monitor and the monitor network.

5. The method for remote breath alcohol monitoring according to claim 1 wherein the first digital image is substantially all of the face of the person providing the first breath sample.

6. The method for remote breath alcohol monitoring according to claim 1 further comprising the steps of:

when the first breath alcohol content is greater than or equal to a predefined value, performing the following steps before sending step (d):
- (c1) generating by the remote breath alcohol monitor an output requesting a retest;
- (c2) receiving a second breath sample in the remote breath alcohol monitor;
- (c3) analyzing the second breath sample for a second breath alcohol content;
- (c4) capturing a second digital image of the face of the person providing the second breath sample;
- (c5) performing a second facial match on a second template extracted from the second digital image compared to the gallery template derived from the gallery of images of the person; and
- (c6) sending by the remote breath alcohol monitor at least one of the second breath alcohol content and the result of the second facial match along with the at least one of the first breath alcohol content and the result of the first facial match to the monitor network.

7. The method for remote breath alcohol monitoring according to claim 6 wherein performing steps (c) and (c5) further comprise the steps of:
comparing the first template to the gallery template derived from the gallery of images, and determining a first match score;
comparing the second template to the gallery template, and determining a second match score;
determining a first facial match for the first digital image if the first match score is greater than a threshold value; or, determining a first facial mismatch if the first match score is equal to or less than the threshold value; and
determining a second facial match for the second digital image if the second match score is greater than the threshold value; or, determining a second facial mismatch if the second match score is equal to or less than the threshold value.

8. The method for remote breath alcohol monitoring according to claim 7 further comprising the step of:
storing the gallery of images of the person and the gallery template of the person in the remote breath alcohol monitor.

9. The method for remote breath alcohol monitoring according to claim 7 further comprising the steps of:
when a facial mismatch is determined, displaying by the remote breath alcohol monitor a series of messages regarding the proper way for the person to give a breath sample that results in a capture of a high quality digital image; and
prompting the person to retake a breath test.

10. The method for remote breath alcohol monitoring according to claim 7 further comprising the steps of:
capturing with the remote breath alcohol monitor an enrollment digital image of the at least a portion of the face of the person providing an enrollment breath sample; and
extracting an enrollment template from the enrollment digital images of the person.

11. The method for remote breath alcohol monitoring according to claim 10 further comprising the steps of:
capturing with the remote breath alcohol monitor a series of additional digital images of the at least a portion of the face of the person providing a series of additional breath samples;
extracting a series of additional templates from the series of additional digital images of the person; and
recalculating the gallery template as a function of the enrollment template and the series of additional templates.

12. The method for remote breath alcohol monitoring according to claim 6 wherein capturing steps (b) and (c4) further comprise the steps of:
generating a first quality score for the first digital image;
generating a second quality score for the second digital image;
performing the first facial match if the first quality score is greater than a threshold value; and
performing the second facial match if the second quality score is greater than the threshold value.

13. The method for remote breath alcohol monitoring according to claim 6 further comprising the steps of:
capturing a first location fix at a time of receiving the first breath sample;
capturing a second location fix at a time of receiving the second breath sample;
sending the first location fix to the monitor network along with the at least one of the first breath alcohol content and the result of the first facial match; and
sending the second location fix to the monitor network along with the at least one of the second breath alcohol content and the result of the second facial match.

14. The method for remote breath alcohol monitoring according to claim 6 further comprising the steps of:
performing by the remote breath alcohol monitor a communication with the monitor network;
downloading from the monitor network an on-demand breath test request to the remote breath alcohol monitor;
generating by the remote breath alcohol monitor an output requesting a breath test; and
repeating steps (a) through (c6) for a next breath sample.

15. A method for remote breath alcohol monitoring comprising the steps of:
- (a) enrolling an offender by gathering enrollment data, the enrolling step further comprising the steps of:
  - (a1) capturing with a remote breath alcohol monitor an enrollment image of at least a portion of a face of the offender;
  - (a2) extracting a first template from the enrollment image, wherein the first template becomes a gallery template stored in the remote breath alcohol monitor, wherein subsequent templates extracted from subsequent captured images of the at least a portion of a face of the offender are added to recalculate the gallery template as a function of the first template of the enrollment image of the face of the offender and the subsequent templates of captured images of the at least a portion of the offender;
- (b) providing the remote breath alcohol monitor with a testing schedule for the offender;
- (c) prompting the offender by the remote breath alcohol monitor to take a breath test; and
- (d) sending a result of the breath test to a monitor network.

16. The method for remote breath alcohol monitoring according to claim 15 wherein the capturing step (a1) further comprising the step of:
capturing the enrollment image with a camera in the remote breath alcohol monitor.

17. The method for remote breath alcohol monitoring according to claim 15 further comprising the step of:
analyzing by the monitor network the result of the breath test.

18. The method for remote breath alcohol monitoring according to claim 17 wherein the analyzing step further comprises the steps of:
determining if an immediate notification is required based upon one or more preferences established by a supervising agency;
if the determining if the immediate notification is required step is yes, sending the immediate notification by the monitor network to the supervising agency;
if the determining if the immediate notification is required step is no, determining if any changes to the testing schedule are required; and
if the determining if any changes to the testing schedule are required step is yes, downloading the changes to the testing schedule to the remote breath alcohol monitor.

19. The method for remote breath alcohol monitoring according to claim 17 wherein the analyzing step further comprises the step of:
analyzing a result of a facial match, a breath alcohol content, and a location fix.

20. The method for remote breath alcohol monitoring according to claim 19 wherein the analyzing step further comprises the steps of:
when the result of the facial match is a fail, displaying by the remote breath alcohol monitor a series of messages regarding the proper way for the offender to give a breath sample that results in a capture of a high quality digital image; and
prompting the offender by the remote breath alcohol monitor to retake a breath test.

21. The method for remote breath alcohol monitoring according to claim 15 further comprising the step of:
tailoring the testing schedule to the offender to include at least one of a set schedule, a random schedule, a flexible schedule, and on-demand testing.

22. The method for remote breath alcohol monitoring according to claim 15 wherein prompting step (c) further comprises the steps of:
when the offender fails to take the breath test when prompted, capturing a location fix; and
sending by the remote breath alcohol monitor the location fix to the monitor network.

23. A remote breath alcohol monitor comprising:
an opening in the remote breath alcohol monitor configured to convey a breath sample to an ethanol sensor within the remote breath alcohol monitor;
at least one circuit board assembly within the remote breath alcohol monitor configured to process an output of the ethanol sensor to determine a breath alcohol content;
a camera connected to the at least one circuit board assembly configured to capture a facial image of a person, wherein the at least one circuit board assembly compares a first template extracted from the facial image of the person a gallery template derived from a gallery of images of the person; and
a transmitter connected to the at least one circuit board assembly configured to send at least a one of the breath alcohol content and the facial image to a monitor network.

24. The remote breath alcohol monitor according to claim 23, wherein the transmitter is a wireless cellular phone module.

25. The remote breath alcohol monitor according to claim 23 further comprising:
an Ethernet port, wherein the at least one of the breath alcohol content and the facial image of the person are sent to the monitor network through the Ethernet port over one or more Ethernet links.

26. The remote breath alcohol monitor according to claim 23 further comprising:
a memory in the at least one circuit board assembly for storing a schedule for taking breath tests, wherein when a scheduled breath test time arrives, the remote breath alcohol monitor will turn itself on and outputs a prompt to take a breath test.

27. The method for remote breath alcohol monitoring according to claim 1 further comprising the step of:
extracting the first template from the first digital image of the person by formulating a mathematical model that reflects a one or more characteristics of the at least a portion of a face of a person captured in the first digital image.

28. The method for remote breath alcohol monitoring according to claim 27 wherein the one or more characteristics of the at least a portion of a face of a person captured in the first digital image are selected from the group consisting of:
a distance between a first pupil and a second pupil;
a shape of a face;
a location of a nose and a mouth with respect to each other and the first and second pupils;
a shape of a first eye; and
a shape of a second eye.

29. The method for remote breath alcohol monitoring according to claim 27 further comprising the step of:
calculating the gallery template as a function of a plurality of templates extracted from a plurality of images of the at least a portion of a face of a person.

30. The method for remote breath alcohol monitoring according to claim 15 wherein the extracting the first template from the enrollment image step (a2) further comprises the step of:
formulating a mathematical model that reflects a one or more characteristics of the first enrollment image of the at least a portion of a face of the offender.

31. The remote breath alcohol monitor according to claim 30 wherein the one or more characteristics of the first enrollment image of the at least a portion of a face of the offender are selected from the group consisting of:
a distance between a first pupil and a second pupil;
a shape of a face;
a location of a nose and a mouth with respect to each other and the first and second pupils;
a shape of a first eye; and
a shape of a second eye.

32. The remote breath alcohol monitor according to claim 23, wherein the first template is a mathematical model that reflects a one or more characteristics of the facial image of the person.

33. The remote breath alcohol monitor according to claim 32, wherein the one or more characteristics are selected from the group consisting of;
a distance between a first pupil and a second pupil;
a shape of a face;
a location of a nose and a mouth with respect to each other and the first and second pupils;
a shape of a first eye; and
a shape of a second eye.

34. The remote breath alcohol monitor according to claim 32, wherein the gallery template is calculated as a function of a plurality of templates extracted from a plurality of facial images of the person.

* * * * *

UNITED STATES PATENT AND TRADEMARK OFFICE
CERTIFICATE OF CORRECTION

PATENT NO. : 9,829,480 B2
APPLICATION NO. : 14/658593
DATED : November 28, 2017
INVENTOR(S) : Wojcik et al.

Page 1 of 1

It is certified that error appears in the above-identified patent and that said Letters Patent is hereby corrected as shown below:

In the Claims

Column 26,
Line 53, Claim 15, Add the words – of the face – after the word "portion" and before the word "of".

Signed and Sealed this
Thirteenth Day of February, 2018

Andrei Iancu
*Director of the United States Patent and Trademark Office*